United States Patent
Ting et al.

(10) Patent No.: US 7,919,505 B2
(45) Date of Patent: Apr. 5, 2011

(54) XINAFOATE SALT OF A SUBSTITUTED 5-OXAZOL-2-YL-QUINOLINE COMPOUND

(75) Inventors: Pauline C. Ting, New Providence, NJ (US); Joe F. Lee, Brooklyn, NY (US); Kung-I Feng, Basking Ridge, NJ (US); Michael R. Reeder, Skillman, NJ (US); Scott T. Trzaska, Raritan, NJ (US); Man Zhu, Clark, NJ (US); Chen Mao, New Providence, NJ (US); Dimitar L. Filipov, Elizabeth, NJ (US); Dimitrios N. Zarkadas, Fanwood, NJ (US)

(73) Assignee: Schering Corporation, Kenilworth, NJ (US)

( * ) Notice: Subject to any disclaimer, the term of this patent is extended or adjusted under 35 U.S.C. 154(b) by 875 days.

(21) Appl. No.: 11/775,383

(22) Filed: Jul. 10, 2007

(65) Prior Publication Data
US 2008/0027101 A1 Jan. 31, 2008

Related U.S. Application Data

(60) Provisional application No. 60/830,057, filed on Jul. 11, 2006.

(51) Int. Cl.
C07D 215/38 (2006.01)
A61K 31/04 (2006.01)

(52) U.S. Cl. .......................... 514/312; 546/159; 546/163

(58) Field of Classification Search .................. 514/312; 546/159, 163
See application file for complete search history.

(56) References Cited

U.S. PATENT DOCUMENTS

| | | | |
|---|---|---|---|
| 5,270,324 A | 12/1993 | Zamboni | |
| 5,296,495 A | 3/1994 | Matsuo | |
| 5,352,707 A | 10/1994 | Pompni | |
| 5,472,964 A | 12/1995 | Young | |
| 5,804,588 A | 9/1998 | Dyke | |
| 5,834,485 A | 11/1998 | Dyke | |
| 6,069,151 A | 5/2000 | Dyke | |
| 7,511,062 B2* | 3/2009 | Kuang et al. | 514/312 |
| 2005/0017134 A1 | 1/2005 | Hooper | |

FOREIGN PATENT DOCUMENTS

| | | | |
|---|---|---|---|
| WO | 2005/116009 | * | 12/2005 |
| WO | WO 2005/116009 A1 | | 12/2005 |
| WO | WO 2006/105401 A2 | | 10/2006 |

OTHER PUBLICATIONS

West al., "Identification of Two $H_3$-Histamine Receptor Subtypes", Molecular Pharmacology, 38: 610-613 (1990).
PCT International Search Report dated Jan. 21, 2008 for PCT Application No. PCT/US2007/015715.

* cited by examiner

*Primary Examiner* — D. Margaret Seaman
(74) *Attorney, Agent, or Firm* — Patricia A. Shatynski; Valerie J. Camara

(57) ABSTRACT

The present invention relates to the compound of the formula

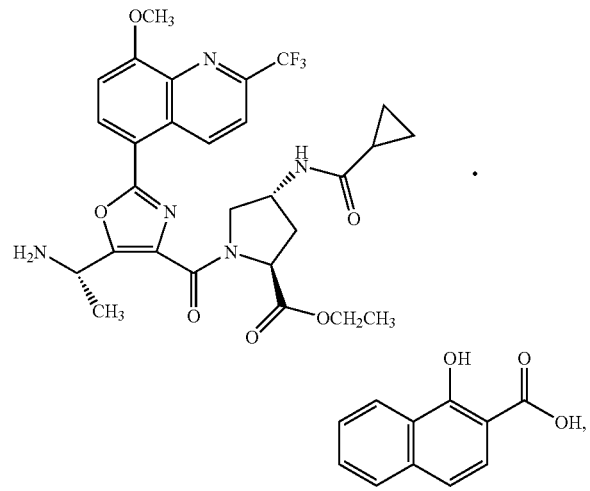

To methods of treating upper and lower obstructive airway diseases using said compound, to formulations comprising it, and to polymorphs and processes of synthesis of the polymorphic forms.

44 Claims, 11 Drawing Sheets

XINAFOATE SALT OF A SUBSTITUTED 5-OXAZOL-2-YL-QUINOLINE COMPOUND

This application claims the benefit of U.S. Provisional Application No. 60/830,057, filed Jul. 11, 2006, which is incorporated herein by reference in its entirety,

FIELD OF THE INVENTION

The present invention relates to the xinafoate salt of 1-[[5-(1(S)-aminoethyl)-2-[8-methoxy-2-(trifluoromethyl)-5-quinolyl]-4-oxazolyl]carbonyl]-4(R)-[(cyclopropyl-carbonyl)amino]-L-proline, ethyl ester, pharmaceutical compositions comprising said salt, and methods of treating upper and lower obstructive diseases of the airways by inhalation of said salt.

BACKGROUND OF THE INVENTION

Phosphodiesterases are known to regulate cyclic AMP, and phosphodiesterase 4 (PDE4) has been shown to be the predominant regulator of cyclic AMP in respiratory smooth muscle and inflammatory cells. Inhibitors of PDE4 are useful in treating a variety of diseases, including allergic and inflammatory diseases, diabetes, central nervous system diseases, pain, and viruses that produce TNF.

Amino-substituted quinolyl PDE4 inhibitors are disclosed in U.S. Pat. No. 5,804,588; sulfonamide-substituted quinolyl PDE4 inhibitors are disclosed in U.S. Pat. No. 5,834,485; and (benzo-fused)heteroaryl-substituted PDE4 inhibitors are disclosed in U.S. Pat. No. 6,069,151. Oxazolyl-substituted quinolyl PDE4 inhibitors are disclosed in PCT/US2005/017134.

The compound referred to as Compound A herein, is described as its free base and pharmaceutically acceptable salt forms in WO2005/116009A1 on page 95, Example 26-347 and on page 228, claim 19; those descriptions are hereby incorporated by reference.

SUMMARY OF THE INVENTION

This invention provides the xinafoate salt of 1-[[5-(1(S)-aminoethyl)-2-[8-methoxy-2-(trifluoromethyl)5-quinolyl]-4-oxazolyl]carbonyl]-4(R)-[(cyclopropyl-carbonyl)amino]-L-proline, ethyl ester. That is, the compound of formula I:

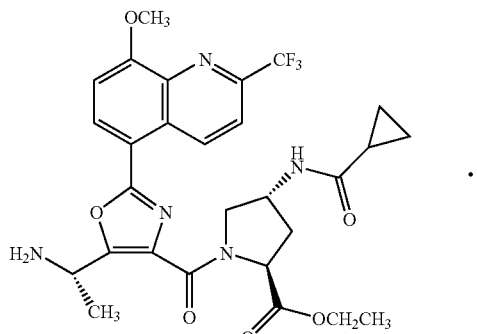

I

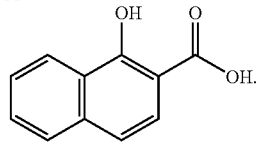

The invention also relates to a method of treating upper or lower obstructive diseases of the airways in a patient in need of such treatment comprising administering to said patient by inhalation an effective amount of the compound of formula 1.

The invention also relates to a method of treating upper or lower obstructive diseases of the airways in a patient in need of such treatment comprising administering to said patient by inhalation an effective amount of a combination of the compound of formula 1 and at least one additional agent useful for treating upper or lower obstructive diseases of the airway. Preferred additional agents are beta-agonists, muscarinic antagonists or corticosteroids.

The invention further relates to an inhalable pharmaceutical composition comprising an effective amount of the compound of formula I.

The invention further relates to an inhalable pharmaceutical composition comprising an effective amount of a combination of the compound of formula 1 and at least one additional agent useful for treating upper or lower obstructive diseases of the airway.

The invention also relates to crystalline polymorphs and pseudopolymorph (hydrate) of the compound of formula I wherein, said polymorph is selected from the group consisting of:

Form 1 that exhibits a powder x-ray diffraction pattern substantially the same as the pattern shown in FIG. 1;

Form 2 that exhibits a powder x-ray diffraction pattern substantially the same as the pattern shown in FIG. 2; and Dihydrate Form 1 that exhibits a powder x-ray diffraction pattern substantially the same as the pattern shown in FIG. 3.

Form 3 that exhibits a powder x-ray diffraction pattern substantially the same as the pattern shown in FIG. 10.

This invention further provides a crystalline polymorph Form 1 of formula I that exhibits a powder x-ray diffraction pattern having characteristic peak locations of 6.1, 7,7, 13.0 and 15.9 degrees 2θ.

In another embodiment, the crystalline polymorph Form 1 of formula I exhibits a powder x-ray diffraction pattern having characteristic peak locations of 5.6, 6.1, 7.7, 13.0, 15.9, 17.8, 18.4 and 26.1 degrees 2θ.

In another embodiment, the crystalline polymorph Form 1 of formula I exhibits a powder x-ray diffraction pattern having characteristic peak locations of 5.6, 6.1, 7.7, 9.2, 13.0, 14.2, 15.9, 17.8, 18.4, 20.5, 22.9 and 26.1 degrees 2θ.

This invention further provides a crystalline polymorph Form 2 of formula I that exhibits a powder x-ray diffraction pattern having characteristic peak locations of 10.6, 13.6, 19.1, and 21.2 degrees 2θ.

In another embodiment, the crystalline polymorph Form 2 of formula I exhibits a powder x-ray diffraction pattern having characteristic peak locations of 10.6, 13.6, 17.9, 18.8, 19.1, 20.2, 21.2 and 23.9 degrees 2θ.

In another embodiment, the crystalline polymorph Form 2 of formula I exhibits a powder x-ray diffraction pattern having characteristic peak locations of 9.4, 10.6, 13.6, 17.9, 18.8, 19.1, 20.2, 21.2, 23.9, 26.0, 26.6 and 28.1 degrees 2θ.

This invention further provides a crystalline Dihydrate Form 1 of formula I that exhibits a powder x-ray diffraction pattern having characteristic peak locations of 8.2, 16.5, 18.5, and 24.9 degrees 2θ.

In another embodiment, the crystalline Dihydrate Form 1 of formula I exhibits a powder x-ray diffraction pattern having characteristic peak locations of 5.5, 8.2, 14.3, 16.5, 16.9, 18.5, 20.6, and 24.9 degrees 2θ.

In another embodiment, the crystalline Dihydrate Form 1 of formula I exhibits a powder x-ray diffraction pattern having characteristic peak locations of 5.5, 7.2, 8.2, 14.3, 14.7, 16.5, 16.9, 18.5, 20.6, 24.1, 24.9 and 26.8 degrees 2θ.

This invention further provides a crystalline polymorph Form 3 of formula I that exhibits a powder x-ray diffraction pattern having characteristic peak locations of 4.6, 7.9, 12.1, and 18.9 degrees 2θ.

In another embodiment, the crystalline polymorph Form 3 of formula I exhibits a powder x-ray diffraction pattern having characteristic peak locations of 4.6, 7.9, 9.1, 12.1, 13.7, 15.8, 16.5, and 18.9 degrees 2θ.

In another embodiment, the crystalline polymorph Form 3 of formula I exhibits a powder x-ray diffraction pattern having characteristic peak locations of 4,6, 7.9, 9.1, 12.1, 13.7, 15.8, 16.5, 18.9, 20.0, 23.9, 24.3, and 25.7 degrees 2θ.

The invention further provides two processes for preparing the Form 1 polymorph xinafoate salt from Compound A.

First Method:

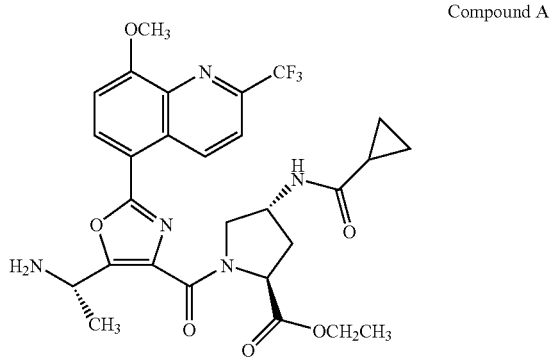
Compound A comprising the steps of:
a) dissolving Compound A in hot ethanol and adding xinafoic acid while continuing to heat the mixture;
b) adding additional ethanol and water, and heating the mixture to near boiling;
c) filtering the hot mixture, then cooling slowly to room temperature and allowing the mixture to stand at room temperature overnight until Form I crystals precipitate; and
d) cooling the filtrate to 0° C. and filtering the Form 1 crystals.

Second Method:

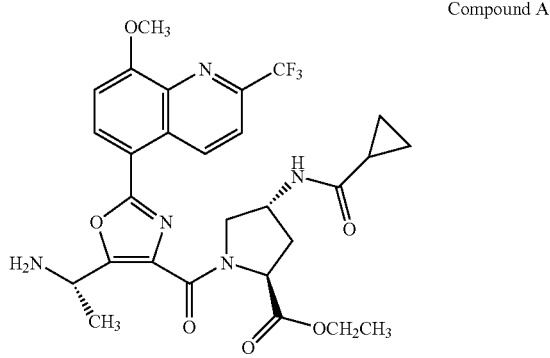
Compound A comprising the steps of:
a) adding toluene and methanol to Compound A and xinafoic acid and mixing, forming a slurry;
b) heating said slurry to about 62° C. while mixing, affording a homogeneous mixture;
c) distilling said homogeneous mixture atmospherically, cooling distilled mixture to about 50° C. seeding said distilled mixture with Compound A Form 1 seeds, resulting in crystals in a slurry;
d) stirring said slurry for about 30 minutes at about 50° C. and cooling the slurry to about 10° C.;
e) adding additional toluene to the cooled slurry and vacuum distilling, then adding additional toluene and stirring for about 20 minutes at about 20° C. forming solid material;
f) collecting resulting solids using agitated dryer under vacuum forming a wet cake; washing said wet cake with toluene and drying at about 50° C. for about 3 hours without agitation, then about 80° C. for about 12 hours with about 20 R.P.M. agitation, then about 80° C. for about 12 hours with about 60 R.P.M. agitation, all under vacuum.

Third Method:

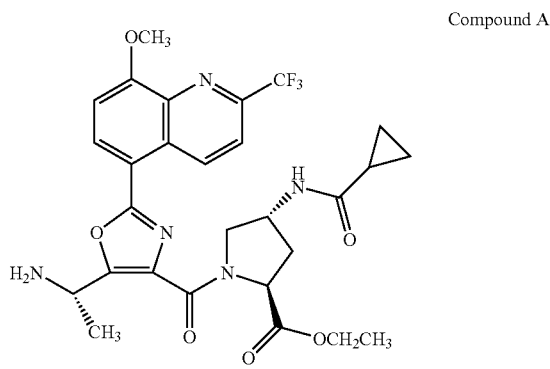
Compound A comprising the steps of:
a) dissolving Compound A and xinafoic acid in hot methanol separately;
b) filtering both of the hot solutions and mixing the two solutions;
c) refluxing the mixture and distilling out the excess methanol; and
d) cooling the mixture to 0C forming a precipitate and filtering the Form 1 crystals.

The invention further provides a crystalline polymorph Form 1 of Compound A that is the product of the above process.

The invention further provides a process for preparing the Form 2 polymorph xinafoate salt from Compound A:

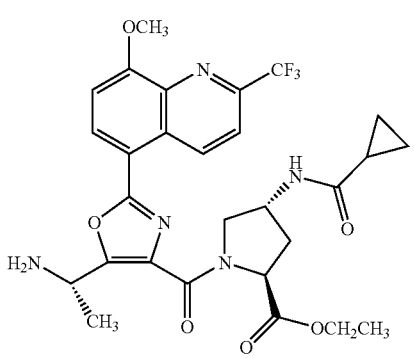

Compound A comprising the steps of:
 a) dissolving Compound A in hot methanol and adding xinafoic acid while continuing to heat the mixture;
 b) adding water, and heating the mixture to near boiling;
 c) filtering the hot mixture, then cooling slowly to room temperature and allowing the mixture to stand at room temperature overnight until Form 2 crystals precipitate; and
 d) cooling the filtrate to 0° C. and filtering the Form 2 crystals.

The invention further provides a crystalline Form 2 polymorph xinafoate salt of Compound A that is the product of the above process.

The invention further provides a process for preparing the Dinydrate Form 1 from Form 1 polymorph xinafoate salt of Compound A:

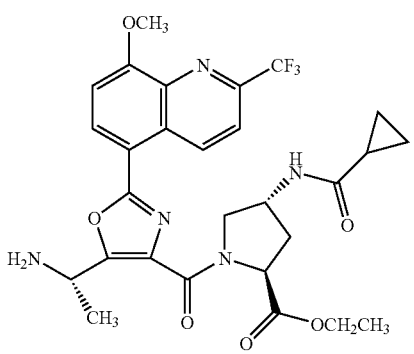

Compound A comprising the steps of:
 a) The addition of water during xinatoate salt formation is necessary to obtain the crystalline form. Suspending Form I polymorph xinafoate salt of Compound A in a mixture of water and methanol;
 b) the suspension was stirred for 21 hours, solids were isolated by centrifugation of the suspension then decanting off the supernatant;
 c) Solids were dried under vacuum at room temperature.

The invention further provides a crystalline Dihydrate Form 2 xinafoate salt of Compound A that is the product of the above process.

The invention further provides a process for preparing the Form 3 polymorph xinafoate salt from Compound A:

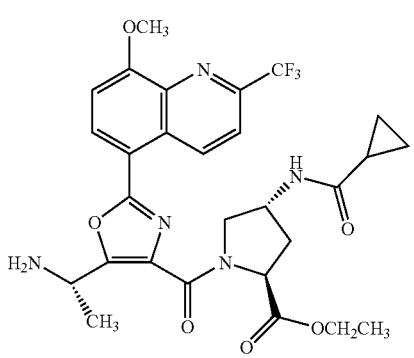

Compound A comprising the steps of:
 a) combining a mixture of compound A and xinafoic acid in 2-propanol;
 b) heat mixture to reflux and add more 2-propanol; hold mixture at reflux for about 1 hour then cooled to room temperature;
 c) filter mixture, wash solids with 2-propanol, dry under vacuum.

The invention further provides a crystalline Form 3 polymorph xinafoate salt of Compound A that is the product of the above process.

The invention further provides a purified form of the Form 1 polymorph of the compound of formula I.

The invention further provides a purified form of the Form 2 polymorph of the compound of formula I.

The invention further provides a purified form of the Dihydrate Form 1 of the compound of formula I.

The invention further provides a purified form of the Form 3 polymorph of the compound of formula I.

The invention also claims a method of treating upper or lower obstructive diseases of the airways in a patient in need of such treatment comprising administering to said patient by inhalation an effective amount of the Form 1 polymorph of the compound of formula I, as well as an inhalable pharmaceutical composition comprising an effective amount of the Form 1 polymorph of the compound of formula I and a pharmaceutically acceptable carrier.

The invention also claims a method of treating upper or lower obstructive diseases of the airways in a patient in need of such treatment comprising administering to said patient by inhalation an effective amount of the Form 2 polymorph of the compound of formula I, as well as an inhalable pharmaceutical composition comprising an effective amount of the Form 2 polymorph of the compound of formula I and a pharmaceutically acceptable carrier.

The invention also claims a method of treating upper or lower obstructive diseases of the airways in a patient in need of such treatment comprising administering to said patient by inhalation an effective amount of the Dihydrate Form 1 of the compound of formula I, as well as an inhalable pharmaceutical composition comprising an effective amount of the Dihydrate Form 1 of the compound of formula I and a pharmaceutically acceptable carrier.

The invention also claims a method of treating upper or lower obstructive diseases of the airways in a patient in need of such treatment comprising administering to said patient by inhalation an effective amount of the Form 3 polymorph of the compound of formula I, as well as an inhalable pharmaceutical composition comprising an effective amount of the Form 3 polymorph of the compound of formula I and a pharmaceutically acceptable carrier.

DETAILED DESCRIPTION

Figure 1:
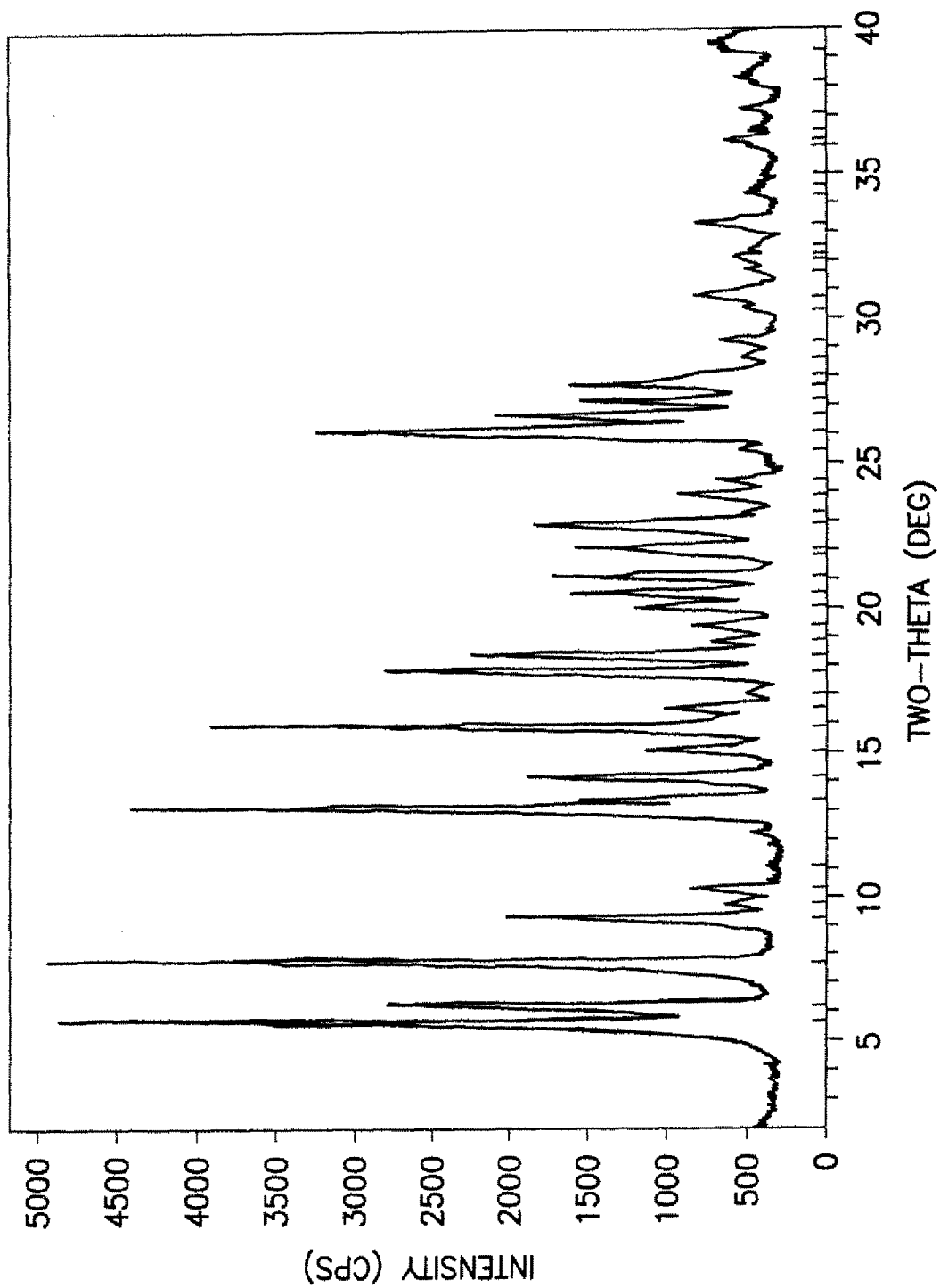
FIG. 1 is a graph of a powder x-ray diffraction (PXRD) pattern of Form 1 of the compound of formula I, generated using an X-ray diffractometer. The graph plots the intensity of the peaks as defined by counts per second versus the diffraction angle 2θ in degrees.
Figure 2:
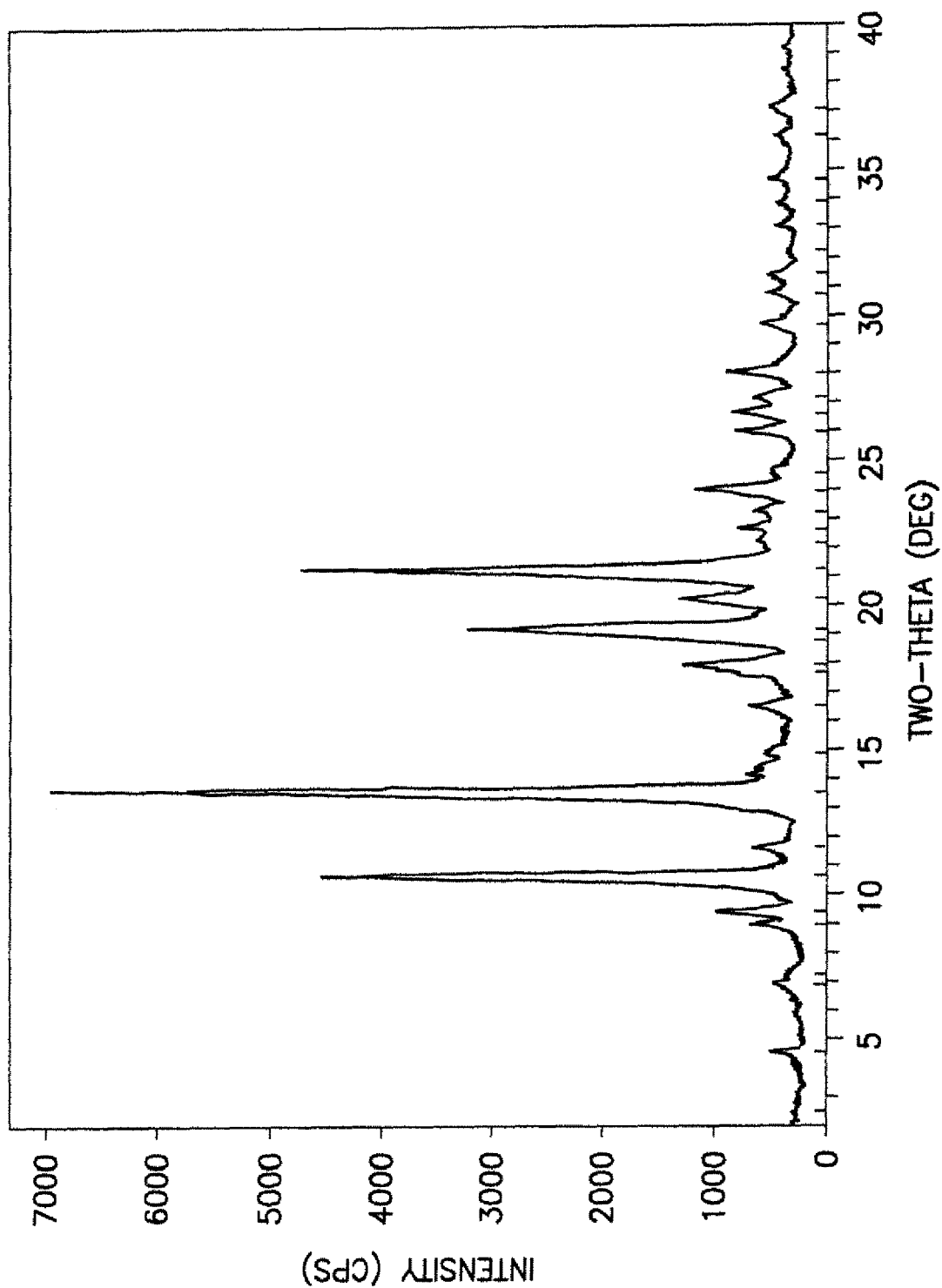
FIG. 2 is a graph of a PXRD pattern of Form 2 of the compound of formula I, generated using an X-ray diffractometer. The graph plots the intensity of the peaks as defined by counts per second versus the diffraction angle 2θ in degrees.

The free base of formula I, hereinafter referred to as Compound A and having the structure

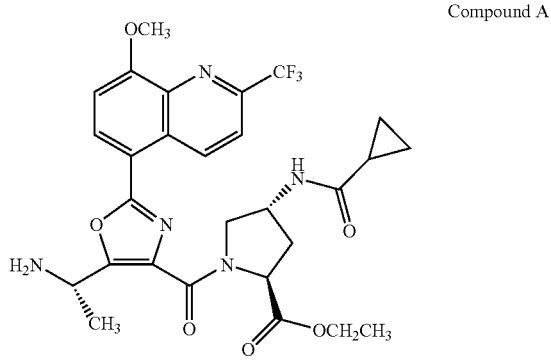

Compound A is disclosed as Example 26-381 in PCT/US2005/017134, incorporated herein by reference.

The compound of formula I, the xinafoate salt of Compound A, is a non-hygroscopic, crystalline salt and exhibits three polymorphs and one hydrate.

The compound of formula I has an unexpectedly superior physical and pharmacokinetic profile for treating upper and lower obstructive diseases of the airways when administered by inhalation compared to Compound A or other salts of compound A. The phosphate, maleate and succinate salts are amorphous; the tartrate is crystalline, but is hygroscopic; the fumarate have crystalline forms, but those forms are unstable hydrates. Thus, the xinafoate salt is unexpectedly superior to other salts for use in an inhaled formulation compared to other salts. Moreover, the xinafoate salt exhibits 25-fold better inhibition of inflammatory cells via intra-trachea administration compared to oral administration.

Three distinct crystalline polymorphs and one hydrate of the compound of formula I were found to exist. These four forms are herein referred to as Forms 1, 2, 3, and Dihydrate Form 1. Since the intended use of this compound is as a therapeutically active pharmaceutical agent, the most stable pharmaceutically acceptable forms of the compound of formula I will be of great interest.

Form 1 is the preferred form for use in the method of this invention.

Polymorphism can be characterized as the ability of a compound to crystallize into different crystal forms, while maintaining the same chemical formula. A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, bioavailability, etc.

As used throughout the specification, the following terms, unless otherwise indicated, shall be understood to have the following meanings:

"Patient" includes both human and other animals.

"Mammal" includes humans and other mammalian animals.

"Polymorph" means a crystalline form of a substance that is distinct from another crystalline form but that shares the same chemical formula.

"Inventive polymorph" means a crystalline polymorph of the compound of formula I.

"Alcohol" means an organic compound containing a hydroxyl group (—OH).

"Excipient" means an essentially inert substance used as a diluent or to give form or consistency to a formulation.

"Effective" or "therapeutically effective" is meant to describe a polymorph of a compound or a composition of the present invention effective as a PDE4 inhibitor and thus producing the desired therapeutic, ameliorative, inhibitory or preventative effect. "Effective amount" or "therapeutically effective amount" is meant to describe an amount of polymorph or a composition of the present invention effective as a PDE4 inhibitor and thus producing the desired therapeutic, ameliorative, inhibitory or preventative effect.

Upper and lower airway obstructive disease treated by the compound of formula I include asthma, COPD (chronic obstructive pulmonary disease), chronic bronchitis, cystic fibrosis, allergic rhinitis, non-allergic rhinitis, rhinosinusitis, adult respiratory disease, acute respiratory distress syndrome, respiratory viruses, cough, interstitial pneumonitis, chronic sinusitis, airflow obstruction, airway hyperresponsiveness (i.e., airway hyperreactivity), bronchiectasis, bronchiolitis, bronchiolitis obliterans (i.e., bronchiolitis obliterans syndrome), dyspnea, emphysema, hypercapnea, hype rinflation, hypoxemia, hyperoxia-induced inflammations, pulmonary fibrosis, pulmonary hypertension, small airway disease, wheeze and colds.

Compounds of formula I are preferably useful in treating asthma, COPD, cough, airflow obstruction, airway hyperresponsiveness (i.e., airway hyperreactivity), bronchiolitis, chronic bronchitis, emphysema, pulmonary fibrosis, pulmonary hypertension, small airway disease, wheeze and allergic rhinitis.

More preferably, compounds of formula I are useful for treating COPD and asthma.

Other agents for treating an obstructive airway disease (e.g., COPD or asthma) for use in combination with the compound of formula I are selected from the group consisting of: steroids (e.g. glucocorticoids), 5-lipoxygenase inhibitors, β-2 adrenoceptor agonists, α-adrenergic receptor agonists, muscarinic M1 antagonists, muscarinic M3 antagonists, muscarinic M2 antagonists, LTB4 antagonists, cysteinyl leukotriene antagonists, bronchodilators, PDE4 inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1, NK2 and NK3 antagonists, GABA-b agonists, nociceptin agonists, expectorants, mucolytic agents, decongestants, mast cell stabilizers, antioxidants, anti-IL-8 antibodies, anti-IL-5 antibodies, anti-IgE antibodies, anti-TNF antibodies, IL-10, adhesion molecule inhibitors, growth hormones and other PDE4 inhibitors.

For use in combination with compounds of formula I, non limitative examples of antihistamines include astemizole, azatadine, azelastine, acrivastine, brompheniramine, certirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, equitazine, mianserin, noberastine, meclizine, norastemizole, picumast, pyrilamine, promethazine, terfenadine, tripelennamine, temelastine, trimeprazine and triprolidine.

Non-limitative examples of histamine $H_3$ receptor antagonists include: thioperamide, impromidine, burimamide, clobenpropit, impentamine, mifetidine, S-sopromidine, R-sopromidine, SKF-91486, GR-175737, GT-2016, UCL-1199 and clozapine. Other compounds can readily be evaluated to determine activity at $H_3$ receptors by known methods, including the guinea pig brain membrane assay and the guinea pig neuronal ileum contraction assay, both of which are described in U.S. Pat. No. 5,352,707. Another useful assay utilizes rat brain membranes and is described by West et al., "Identification of Two-$H_3$-Histamine Receptor Subtypes," *Molecular Pharmacology, Vol.* 38, pages 610-613 (1990).

The term "leukotriene inhibitor" includes any agent or compound that inhibits, restrains, retards or otherwise interacts with the action or activity of leukotrienes. Non-limitative examples of leukotriene inhibitors include montelukast and its sodium salt; 1-(((R)-(3-(2-(6,7-difluoro-2-quinolinyl) ethenyl)phenyl)-3-(2-(2-hydroxy-2-propyl)phenyl)thio) methylcyclopropaneacetic acid, and its sodium salt, described in U.S. Pat. No. 5,270,324; 1-(((1 (R)-3(3-(2-(2,3-dichlorothieno[3,2-b]pyridin-5-yl)-(E)-ethenyl)phenyl)-3-(2-(1-hydroxy-1-methylethyl)phenyl) propyl)thio) methyl) cyclo-propaneacetic acid, and its sodium salt, described in U.S. Pat. No. 5,472,964; praniukast; zafirlukast,; and [2-[[2 (4- ter-butyl-2-thiazolyl)-5-benzofuranyl]oxymethyl]phenyl]acetic acid, described in U.S. Pat. No. 5,296,495.

Non-limitative examples of B-adrenergic receptor agonists include: albuterol, bitolterol, isoetharine, mataproterenol, perbuterol, salmeterol, terbutaline, isoproterenol, ephedrine and epinephrine. Non-limitative examples of α-adrenergic receptor agonists include arylalkylamines, (e.g., phenylpropanolamine and pseudephedrine), imidazoles (e.g,, naphazoline, oxymetazoline, tetrahydrozoline, and xylometazoline), and cycloalkylamines (e.g., propylhexedrine).

A non-limitative example of a mast cell stabilizer is nedocromil sodium. A non-limitative example of an expectorant is guaifenesin. Non-limitative examples of decongestants are pseudoephedrine, phenylpropanolamine and phenylephrine.

Non-limitative examples of other PDE4 inhibitors include roflumilast. theophylline, rolipram, piclamist, cilomilast and CDP-840. Examples of steroids include prednisolone, fluticasone, triamcinolone, beclomethasone, mometasone, budisamide, betamethasone, dexamethasone, prednisone, flunisolide and cortisone.

Non-limitative examples of $NK_1$, $NK_2$ and $NK_3$ tachykinin receptor antagonists include CP-99,994 and SR 48968. Non-limitative examples of muscarinic antagonists include ipratropium bromide and tiatropium bromide.

Non-limitatve examples of $GABA_B$ agonists include baclofen and 3-aminopropyl-phosphinic acid. Dopamine agonists include quinpirole, ropinirole, pramipexole, pergolide and bromocriptine.

"5-lipoxygenase inhibitors" include any agent or compound that inhibits, restrains, retards or otherwise interacts with the enzymatic action of 5-lipoxygenase. Non-limitative examples of 5-lipoxygenase inhibitors include zileuton, docebenone, piripost, ICl-D2318, and ABT 761.

The compound of formula I was prepared by the procedure outlined in Schemes 1 or 2 and detailed in the following Examples 1 or 2. In Example 1 and elsewhere in the application, Et means ethyl, Me means methyl, THF is tetrahydrofuran, DMF is N,N-dimethylformamide, t-BOC and BOC mean t-butoxycarbonyl, RT is room temperature, HATU is N-[(dimethylamino)-1H-1,2,3-triazolo[4,5-b]pyridin-1-yl-methylene]-N-methylmethanaminium hexafluorophosphate N-oxide.

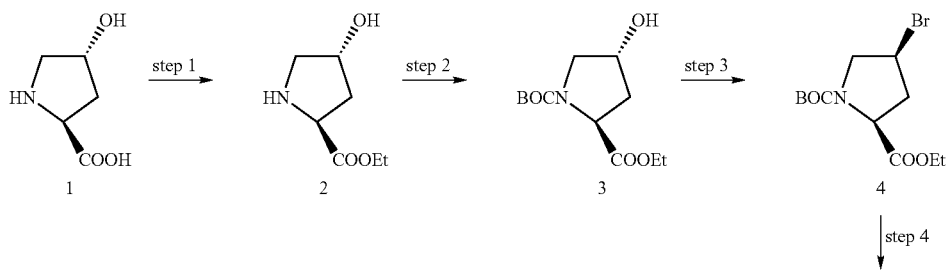

Scheme 1

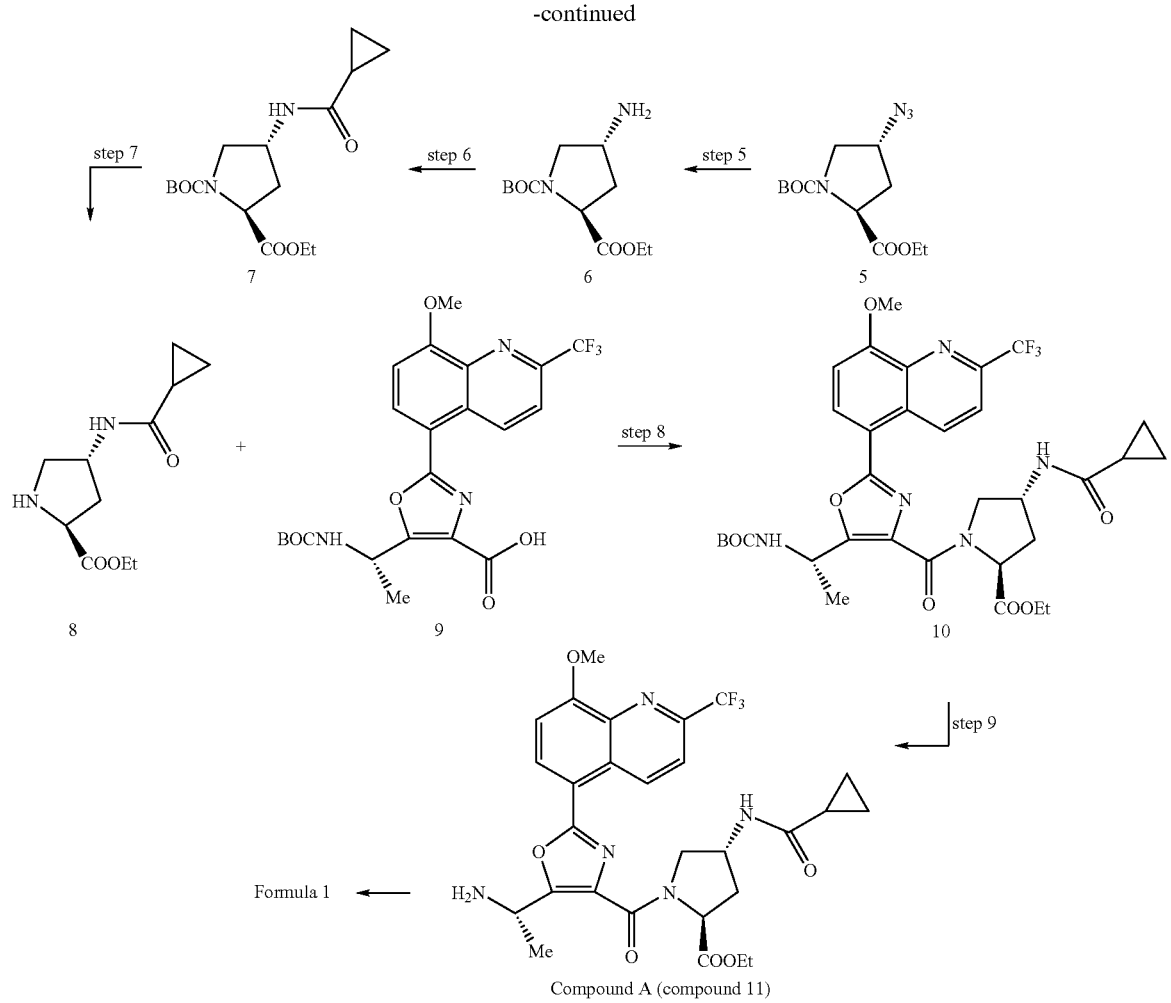

EXAMPLE 1

Step 1:

To a mechanically stirred suspension of compound 1 (100.6 g, 0.767 mol) in EtOH (1000 ml) and cooled to 0° C. was added SOCl$_2$ (136.9 g, 1.15 mol, 84.0 ml) dropwise via addition funnel such that the internal temperature was <15° C. The reaction mixture was heated at reflux for 2.5 h, then cooled to 0° C. Ether (1000 ml) was added, and a white solid precipitated. The solid was isolated by vacuum filtration and washed with ether. The product 2 (HCl salt) was dried in a vacuum oven to give 146.3 g (97%) of a white solid. MS (M+1): m/e 160. $^1$H-NMR (DMSO) δ 1.25 (t, 3H), 2.05 (m, 1H), 2.20 (m, 1H), 3.05 (d, 1H), 3.40 (dd, 1H), 4.20 (q, 2H), 4.45 (m, 2H), 5.65 (broad s, 1 H).

Step 2:

To a solution of compound 2 (HCl salt, 146.2 g, 0.747 mol) dissolved in CH$_2$Cl$_2$ (1600 ml) and EtOH (100 ml) and cooled to 0° C. was added Et$_3$N (113.4 g, 1.12 mol, 156.2 ml). t-BOC anhydride (195.6, 0.90 mol) was added portion-wise. The reaction mixture was stirred at 0° C. for 15 min, then at RT for 16 h. The resulting mixture was concentrated to 800 ml volume and washed with water. The organic solution was dried (MgSO$_4$), filtered, and concentrated. Purification by silica gel chromatography (eluant: 20% EtOAc—CH$_2$Cl$_2$) gave the product 3 (193.7 g, 100%) as a yellow oil. MS (M+Na): m/e 282. $^1$H-NMR (CDCl$_3$) δ 1.30 (t, 3H), 1.45 (s, 9H), 1.75 (m, 1H), 2.10 (m, 1H), 2.30 (m, 1H), 3.45 and 3.55 (d, 1H for two rotamers), 3.65 (dd, 1H), 4.25 (m, 2H), 4.40 and 4.45 (t, 1H for two rotamers), 4.55 (broad s, 1H).

Step 3:

To a solution of compound 3 (36.5 g, 0.141 mol) and triphenyl phosphine (46.2 g, 0.176 mol) dissolved in dry THF (1000 ml) and cooled to 0° C. was added diethyl azodicarboxylate (30.7 g, 0.176 mol) dropwise via addition funnel. The reaction mixture was stirred at 0° C. for 5 min, then LiBr (61.1 g, 0.704 mol) was added in one portion. The resulting mixture was stirred at RT for 16 h. The solvent was evaporated, water (1500 ml) was added, and the aqueous solution was extracted with CH$_2$Cl$_2$. The combined organic extracts was dried (MgSO$_4$), filtered, and concentrated. Purification by silica gel chromatography (eluant: 2% EtOAc—CH$_2$Cl$_2$ to 5% EtOAc—CH$_2$Cl$_2$) gave the product 4 (31.8 g, 70%) as a yellow oil. MS (M+1): mle 322 and 324. $^1$H-NMR (CDCl$_3$) δ 1.30 (m, 3H), 1.45 and 1.50 (s, 9H for two rotamers), 2.45 (m, 1H), 2.85 (m, 1H), 3.75 (m, 1H), 4.05-4.40 (m, 5H).

Step 4:

To a solution of compound 4 (41.2 g, 0.128 mol) dissolved in dry DMSO (300 ml) was added NaN$_3$ (9.15 g, 0.141 mol). The reaction mixture was stirred at RT for 16 h. Water (300 ml) was added, and the aqueous solution was extracted with ether. The combined organic extracts was dried (MgSO$_4$), filtered, and concentrated to give the product 5 (36.4 g, 100%) as an oil. MS (M+Na): m/e 307. ¹H-NMR (CDCl₃) δ 1.30 (t, 3H), 1.45 and 1.50 (s. 9H for two rotamers), 2.20 (m, 1H), 2.35 (m, 1H), 3.50 and 3.60 (m, 1H for two rotamers), 3.75 (m, 1H), 4.15-4.45 (m, 4H).

Step 5:

To a solution of compound 5 (36.4 g, 0.128 mol) dissolved in THF (800 ml) was added 10% palladium on carbon catalyst (10.0 g). The reaction mixture was shaken on a Parr shaker under 40 psi of hydrogen pressure for 16 h. The catalyst was removed by filtration and washed with isopropanol. The filtrate was concentrated. Purification by silica gel chromatography (eluant: CH₂Cl₂ then 10% MeOt with NH₃—CH₂Cl₂) gave the product 6 (24.2 g, 73%) as a light gray solid. MS (M+1): mle 259. ¹H-NMR (CDCl₃) δ 1.30 (t, 3H), 1.45 and 1.50 (3, 9H for two rotamers), 2.00 (m, 1H), 2.15 (m, 1H), 3.10 and 3.20 (m, 1H for two rotamers), 3.70 (m, 2H), 4.20 (m, 2H), 4.35 and 4.40 (m, 1H for two rotamers).

Step 6:

To a solution of compound 6 (12.0 g, 0.0464 mol) dissolved in dry CH₂Cl₂ (300 ml) was added Et₃N (9.4 g, 0.093 mol. 13.0 ml) then cyclopropanecarbonyl chloride (5.3 g, 0.051 mol, 4.64 ml). The reaction mixture was stirred at RT for 16 h. Water (200 ml) was added, and the aqueous solution was extracted with CH₂Cl₂. The combined organic extracts was dried (MgSO₄), filtered, and concentrated. Purification by silica gel chromatography (eluant: 5% MeOH with NH₃—CH₂Cl₂) gave the product 7 (14.3 g, 94%) as an oil. MS (M+Na): mle 349. ¹H-NMR (CDCl₃) δ 0.75 (d, 2H), 1.00 (broad s, 2H), 1.30 (t, 3H), 1.35 (m, 1H), 1.45 and 1.50 (s, 9H for two rotamers), 2.25 and 2.30 (m, 2H for rotamers), 3.30 and 3.45 (dm, 1H for rotamers), 3.80 (m, 1H), 4.15-4.45 (m, 3H), 4.55 (m, 1H), 5.95 and 6.10 (broad singlet, 1H for rotamers).

Step 7:

To a solution of compound 7 (40.0 g, 0.123 mol) dissolved in CH₂Cl₂ (550 ml) was added 4 N HCl in dioxane (153 ml, 0.613 mol). The reaction mixture was stirred at RT for 4 h then concentrated to give the product 8 (32.2 g, 100%) as a colorless foam. MS (M+1): m/e 227. ¹H-NMR (CDCl₃) δ 0.75 (d, 2H), 0.90 (m, 2H), 1.30 (t, 3H), 1.55 (m, 1H), 2.35 (m, 1H), 2.55 (m, 1H), 3.70 (m, 2H), 4.25 (m, 2H), 4.75 (m, 2H), 8.35 (d, 1H), 9.05 (broad s, 1H).

Figure 3:
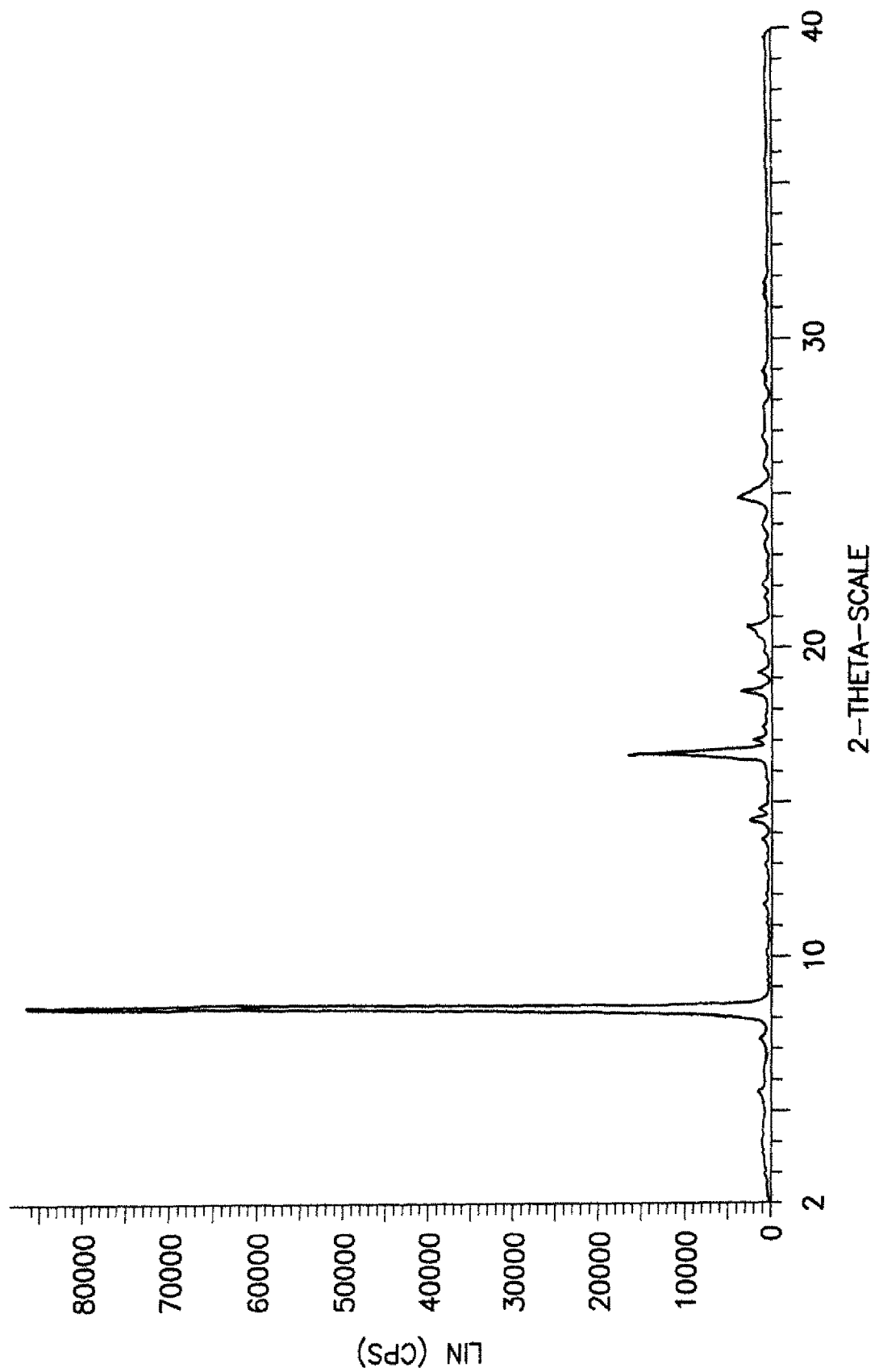
FIG. 3 is a graph of a PXRD pattern of Dihydrate Form 1 of the compound of formula I, generated using an X-ray diffractometer The graph plots the intensity of the peaks as defined by counts per second versus the diffraction angle 2θ in degrees.

Step 8:

To a mixture of compound 8 (5.5 g, 20.8 mmol) and carboxylic acid 9 (10.0 g, 20.8 mmol) in dry DMF (300 ml) was added 3 A sieves (10.0 g), Et₃N (6.3 g, 62.3 mmol, 8.7 ml), then HATU (15.8 g, 41.6 mmol). The reaction mixture was stirred at RT for 21 h then the solvent was concentrated. Water (400 ml) was added, and the aqueous solution was extracted with CH₂Cl₂. The combined organic extracts were dried (MgSO₄), filtered, and concentrated. Purification by silica gel chromatography (eluant: 20% EtOAc—CH₂Cl₂ to 60% EtOAc—CH₂Cl₂) gave the product 10 (14.0 g, 98%) as a colorless foam. MS (M+1): m/e 690. See FIG. 3 for the NMR spectrum.

Figure 4:
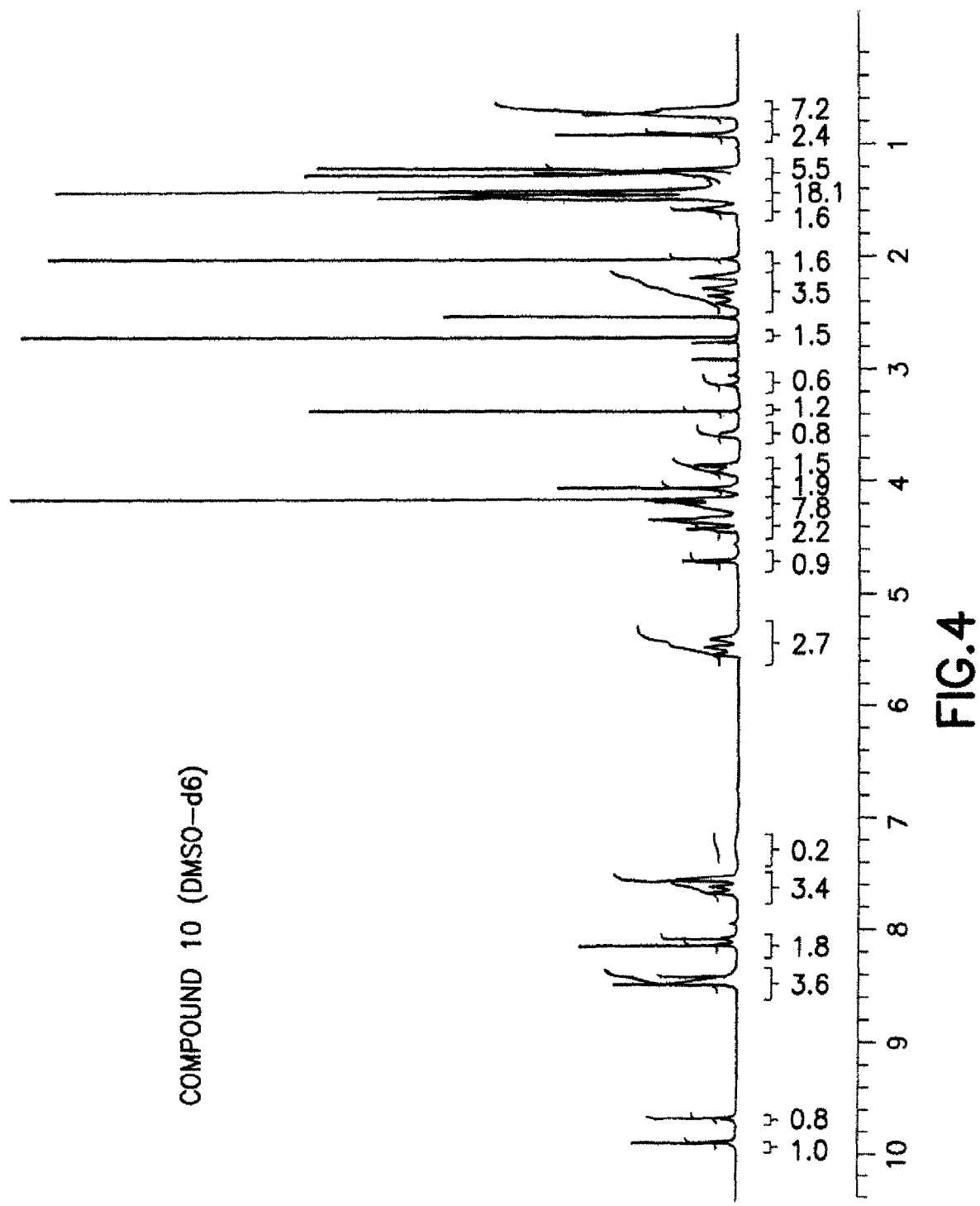
FIG. 4 is a copy of the NMR spectrum of compound 10, the product of Step 8.
Figure 5:
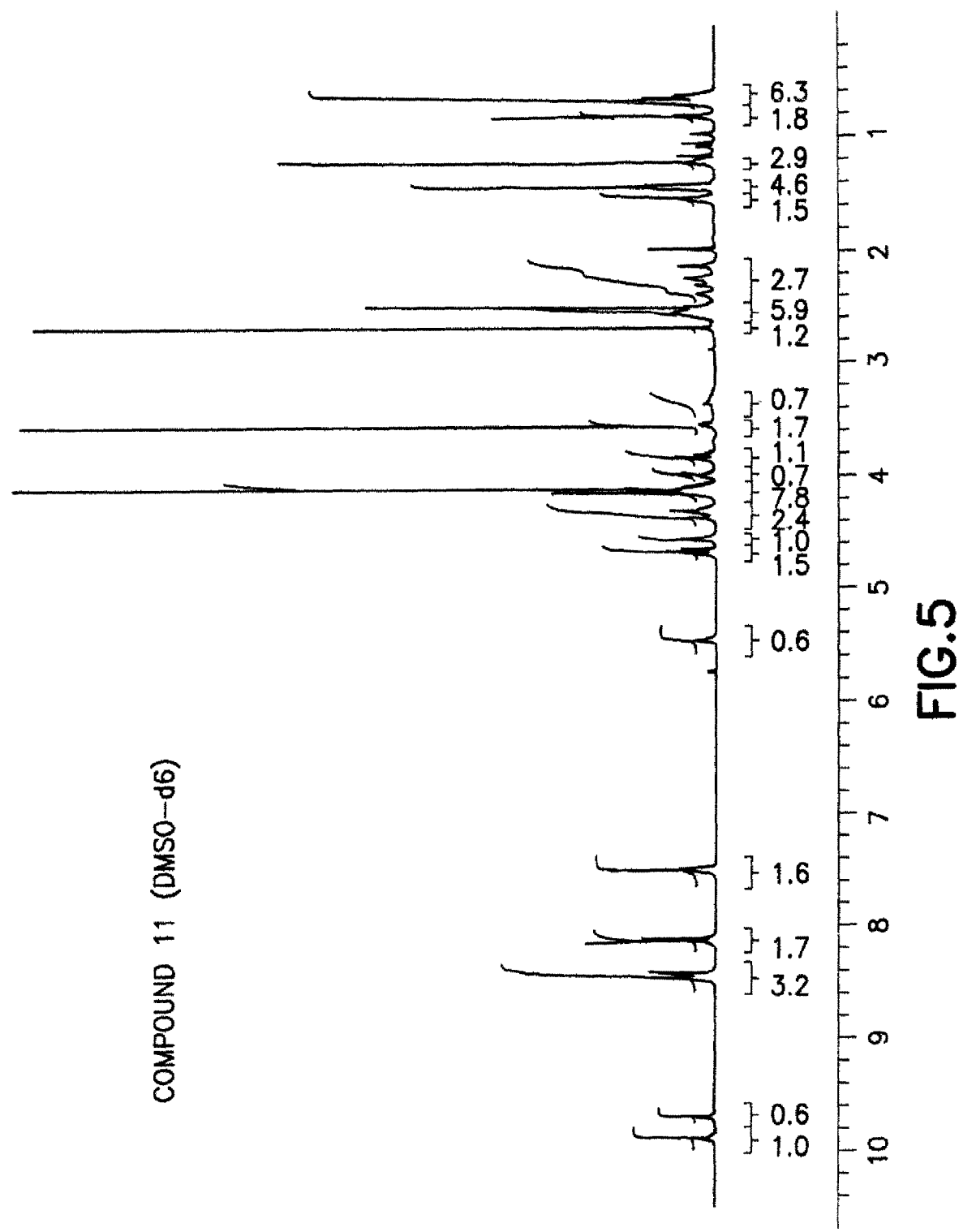
FIG. 5 is a copy of the NMR spectrum of compound 11, also referred to as Compound A.

Step 9:

To a solution of compound 10 (42.1 g, 0.061 mol) dissolved in CH₂Cl₂ (600 ml) and cooled to 0° C. was added 4 N HCl in dioxane (76 ml, 0.305 mol). The reaction mixture was then stirred at RT for 5 h and then concentrated. The crude product was dissolved in 1:1 EtOH:H₂O (120 ml) and made basic (pH=9-10) with 25% aqueous NaOH. CH₂Cl₂ (700 ml) was added, and the reaction mixture was stirred until all solids dissolved. The layers were separated, and the aqueous solution was extracted with CH₂Cl₂. The combined organic extracts was washed with brine, dried (MgSO₄), filtered, and concentrated. Additional CH₂Cl₂ was added, and the mixture was concentrated again. Ether was added, and the mixture was concentrated to give compound 11 (Compound A) (34.4 g, 96%) as a light yellow solid. MS (M+1): m/e 590. See FIG. 4 for the NMR spectrum.

In Example 2 and elsewhere in the application, Et means ethyl, Me means methyl, ETOH means ethanol, NMR means Nuclear Magnetic Resonance, THF is tetrahydrofuran, DMF is N,N-dimethylformamide, t-BOC and BOC mean t-butoxycarbonyl, RT is room temperature, DMSO means dimethyl sulfoxide, Et₃N means triethylamine, NaHMDS is sodiumbis (trimethylsilyl)amide, HOBT is hydroxybenztriazole, EDCl HCl is 1-ethyl-3-[3-dimethylamino)propyl]-carbodimide hydrochloride, NMP is N-methylpyrrolidinone, ca is circa (about), KF is Karl Fisher, and EtOAc is ethyl acetate.

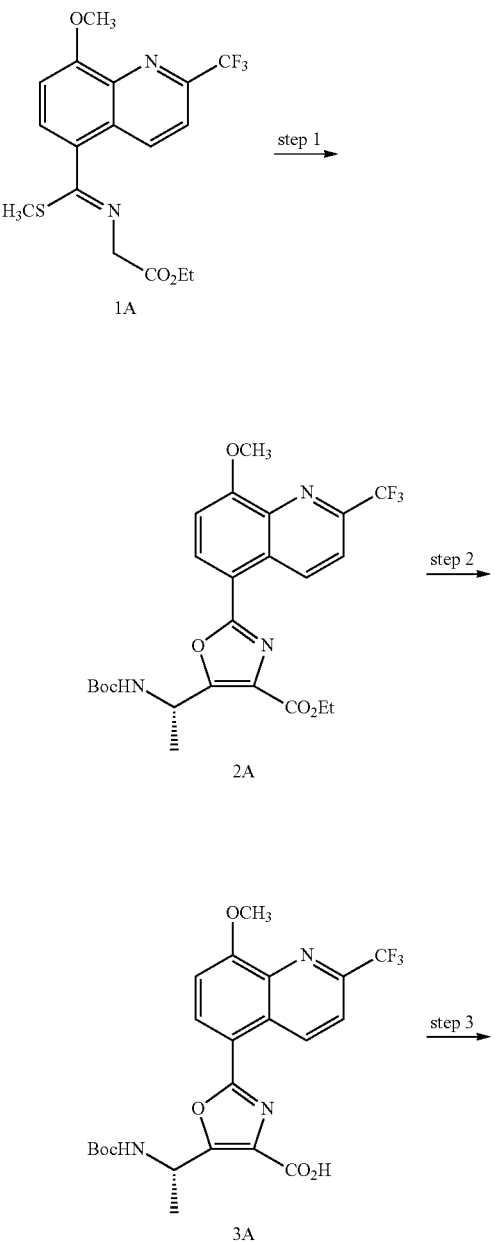

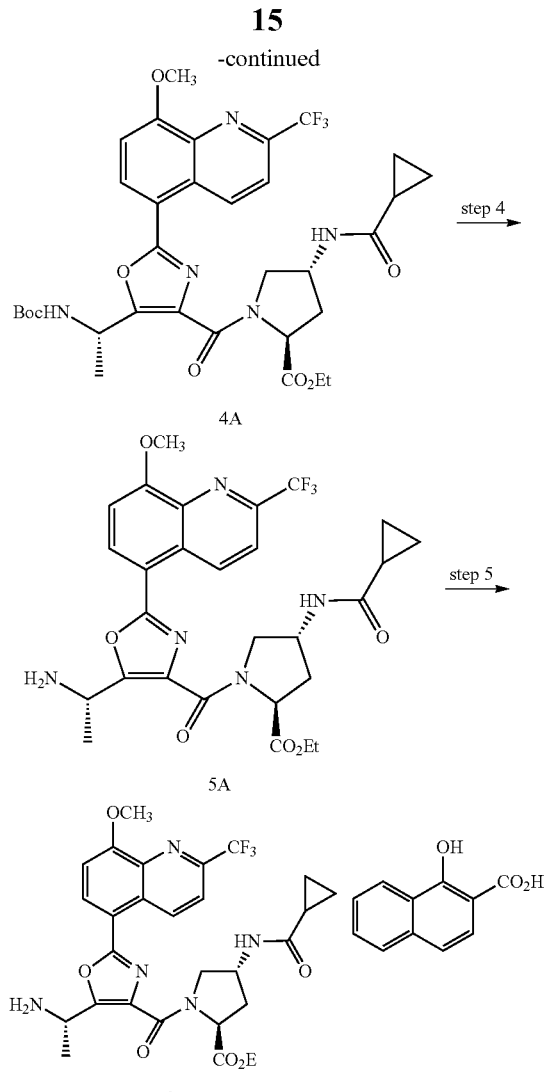

EXAMPLE 2

Step 1:

(S)-2-tert-butoxycarbonylamino-propionic acid, 8.8 kg (46.5 moles, 2 eq), was charged in a 50 L Hastelloy reactor equipped with a thermocouple, $N_2$ inlet and feed tank. Dry tetrahydrofuran (90 liters) (THF, KF<0.005%) was added to the batch and charged to dissolve. Dicyclohexylamine, 8.5 kg (46.9 moles, 2 eq), was added to the batch and slowly charged over about 30 minutes at a temperature range between −5 and 5° C. The batch was agitated for about 15 minutes at a temperature range between −5 and 5° C. Trimethylacetylchloride, 5.7 kg (47.3 moles, 2 eq), was added to the batch and slowly charged over about 30 minutes at a temnperature range between −5 and 5° C. The batch was agitated for about 3 hours at a temperature range between −5 and 5° C. Heptane (27 liters) was added to the batch and charged, followed by 4.5 kg of celite. The batch was filtered under Na, and a filter cake was washed with 30% v/v THF in heptane. The filtrate was concentrated. The filtrate and washes contained the batch under vacuum to a batch volume of about 36 liters. THF (27 liters) was added to the batch and charged. The temperature of the batch was adjusted to about 20 to 3000. The batch was sampled for KF (<0.06 ppm). The batch was a mixed anhydride THF solution and was used in the next step without further purftication.

The coxpound (1A), 9.0 kg (23.3 moles, 1 eq), was charged in a 50 gallon glass lined reactor equipped with a thermocouple, $N_2$ inlet and feed tank DC tetrahydrofuran was added to the batch, 126 liters (THF, KF<0.05%) and was charged to dissolve. The batch was concentrated at 1 atmosphere to a batch volume of about 81 liters. The temperature was adjusted to about −60 to −70° C. NaHMDS (2M in THF, 2.70 kg, 5.9 moles, 0.25 eq) was added and charged over about 15 minutes at a temperature range between −60 and −70° C. The batch was agitated at a temperature range between −60 and −70° C. for about 5 minutes. The mixed anhydride in THF solution (0.83 kg active, 3,2 moles, 0.14 eq) from above was added and was charged over about 15 minutes at a temperature range between −60 and −70° C. The batch was agitated at a temperature range between −60 and −70° C. for about 10 minutes. The sequence of two charges (NaHMDS 2M in THF) and the mixed anhydride were repeated seven more times for a total of eight sets of charges or until the conversion was ≧70%. The NaHMDS (2M in THF) continued to be charged followed by the mixed anhydride in the same ratio based on the amount of starting material remaining until the conversion is ≧94%, Slowly, over about 15 minutes, the batch was transferred to an aqueous solution of 13.5 kg $KH_2PO_4$ dissolved in 90 liters $H_2O$ while the batch temperature was maintained below 30° C. Ethyl acetate, (59 liters), was added and charged then agitated for about 15 minutes and the layers allowed to settle. The aqueous layer was extracted with 45 liters of ethyl acetate. The combined organic layers were washed two times with 32 liters 10% aqueous w/v NaCl. The organic layers was concentrated as a batch at 1 atmosphere to a batch volume of about 45 liters. Methyltertbutylether (MTBE), 90 liters, was added to the batch and charged. The batch was concentrated at 1 atmosphere to a batch volume of about 54 liters. Methyltertbutylether, 45 liters, was charged at a temperature between 55 and 65° C. Heptane, 108 liters, was added to the batch and charged at a temperature between 55 and 65° C. The temperature was adjusted to about 45 to 55° C. and agitated for about 30 minutes. The temperature was then adjusted to about −5 to 5° C. over about 1 hour. The batch was agitated for about 30 minutes at a temperature between −5 and 50C. The batch was filtered forming a filter cake and washed with 33% v/v methyltertbutylether in heptane. The batch was dried in a vacuum oven for at least 12 hours at 45 to 55° C. affording 8.4 kg (72.2%) of compound (2A) as a solid with an ee of >99.0%.

$^1$H NMR (400 MHz, $CDCl_3$): 9.89 (1H, d); 8.56 (1H., d); 7.94 (1H, d); 7.22 (1H, d); 5.91 (1H, s,b); 5.58 (1H, s, b); 4.47 (2H, q); 4.43 (3H, s); 3.75 (2H, t); 1.47 (9H, s); 1.19 (9H, s).

Step 2:

Compound (2A) 20 g (39.3 mmol, 1 eq) was added and charged into a 500 mL three-neck round bottom flask fitted with a mechanical stirrer, an additional funnel and a thermocouple. THF (60 ml), EtOH (20 mL) and water (100 mL) were added to the flask and the reaction mixture was charged. Next, 8 mL of 25% sodium hydroxide solution was added to the reaction mixture and charged. The reaction mixture was agitated at 40° C. for about 4 hours. Upon judging the reaction complete by HPLC assay, water (100 ml) was added to the mixture and the batch was charged and heated to 50° C. Once at 50° C., 1N HCl solution (30 ml) was added to the batch and charged over 30 minutes. The batch was stirred at this temperature for an additional 30 minutes then another 24 ml of 1N HCl solution was added to the batch and the batch was charged over 30 minutes. Water (60 ml) was added to the batch and the batch was charged over 30 minutes at 50° C., forming a slurry. The resulting slurry was cooled to room temperature for over 1 hour forming a product that was collected by suction filtration, which formed a wet cake. The wet cake was washed with 40 ml solvent mixture of ethanol and water (1/5, v/v). The resulting solids were dried under vacuum at 60° C. for 12 h affording 16.8 g (90%) of compound (3A) as an off white solid.

$^1$H NMR (400 MHz, $d_6$-DMSO): 9.97 (1H, d), 8.42 (1H, d), 8.20 (1H, d), 7.48 (1H, d), 5.40 (1H, m), 4.07 (3H, s), 1.45 (3H, d), 1.30 (9H, s)

Step 3:

Part A (2R, 4S)-4(cyclopropanecarbonyl-amino)-pyrrolidine-1,2-dicarboxylic acid-1-tert-butyl ester 2-ethyl ester (BP) (60 g, 184 mmol, 1 eq) was dissolved in EtOAc (1.2L) and a sample was taken as a HPLC standard for 100%. The batch was cooled to 20-35 ° C. and HCl(g) (36 g, 980 mmol, 5.3 eq) was added to the batch and charged while the reaction temperature was maintained between 20-35° C. The HCl salt of the product precipitated as the reaction proceeded. At end of HCl charge, the batch was heated to 20-30° C. and agitated for 1 h. After 1 h. the reaction was checked for completion by sampling the reaction mixture and comparing the HPLC area response of the reaction to the standard above. The reaction was sampled until the amount of BP relative to standard is ≦0.5% area. The batch was concentrated under vacuum at 35-45° C. to 600 mL which formed a thick slurry. NMP (280 mL) was then added to the batch. The batch was concentrated under vacuum at 35-45° C. to a volume of about 560 mL, which formed a clear solution. The clear solution was used directly in the coupling step in Part B.

Part B:

Compound (3) was dissolved in a 1 L 3-neck round bottom flask, (80 g, 166 mmol, 1 eq), HOBT.H$_2$O(28 g, 182 mmol, 1.1 eq) and EDCl.HCl (48 g, 250 mmol, 1.4 eq) in NMP (320 mL) and EtOAc (320 mL). The batch was stirred at 25° C. for 40 min. The solution of BP (from part A) was added to the batch and stirred for 10 min. N-methyl morpholine (80 mL, 724 mmol, 4.4 eq) was added to the reaction at a rate that maintained the temperature below 35° C. Once the reaction was judged complete, EtOAc (320 mL) and water (800 mL) were added to the batch. The resultant batch was stirred 15 min and the layers were separated. The organic layer was washed with 1M HCl (400 mL), then 10% K$_2$CO$_3$ (400 mL) and water (400 mL). The organic layer was concentrated to ~160 mL and acetone (800 mL) was added to the organic layer. Concentrate the batch again to ~240 mL at ~40-50° C. under reduced pressure. Dilute the reaction with another 800 mL of acetone and concentrate the batch to ~240 mL @ 40-50° C. under reduced pressure. The batch temperature was maintained at ~40° C. and 800 mL of heptanes was slowly added to the batch, which resulted in some solids forming. The product solids were collected by filtration and dried under vacuum at 50° C. for 12 h to afford (103 g, 90%) of compound (4A) as an off white solid.

NMR (400 MHz, $d_6$-DMSO): 9.55, 9.03, 8.18, 7.90, 7.77, 7.66 7.10, 7.04, 6.70, 6.66, 6.10, 5.76, 5.36, 4.91, 4.80, 4.4-3.5, 2.58, 2.30, 1.82, 1.56, 1.47, 1.31, 1.07, 1.001.84, 0.74. Note: due to the presence of rotomers, the observed peaks are listed as observed only.

Step 4:

Compound (4A) (20 g, 29 mmol, 1 eq) was added a flask and charged to dissolve in THF (60 ml) and the solution was cooled to 0-10° C. Concentrated HCl (20 ml) was added slowly to maintain the temperature at 0-20° C. At the end of the charge, the solution was warmed to 20-30° C. and agitated for about 4 h at which time the reaction was determined to be complete by HPLC analysis. The batch was diluted with 2-Me-THF (120 ml) and THF (40 ml) and the reaction was quenched with 20% K$_2$CO$_3$ (110 ml) to achieve a pH of 8-8.5. After adjusting the pH, more water (80 ml) was added and the batch was heated to about 30° C. to achieve a clean phase split. The batch was settled for about 15 min, the lower aqueous layer separated, and the organic layer was washed with water (80 ml). The organic phase was diluted with 2-Me-THF (200 ml) and then concentrated under reflux at atmospheric pressure to about 100 ml. The solid product was observed at this volume. The batch was then cooled to 0-10° C. and filtered leaving a wet cake. The wet cake was washed 2 times with 2-Me-THF (40 ml each time). The washed wet cake was dried for at least 12 h at 60° C. under vacuum affording 13.50 g (79%) of compound (5A) also referred to as Compound A herein, as a white solid.

$^1$H NMR (spectrum indicates rotomers, only chemical shift is reported, not integration or peak multiplicity; 400 MHz, $d_6$-DMSO) δ 9.82, 9.62, 8.51, 8.38, 8.07, 7.45, 5.46, 4.69, 4.57, 4.33, 4.15, 4.08, 3.99, 3.83, 2.39, 2.26, 2.16, 1.56, 1.44, 1.22, 0.82, 0.69; MSSES+ m/z (relative intensity) 590 (M+H).

Xinafoate Salt Formation:

Polymorph Form 1: Method 1:

To a solution of Compound A (34.4 g, 0.0583 mol) dissolved in hot EtOH (800 ml) was carefully added portionwise xinafoic acid (10.98 g, 0.0583 mol) while continuing to heat the EtOH solution. Additional EtOH (200 ml) and water (6 ml) were added. The reaction mixture was heated to near boiling to dissolve all solids, then filtered. The filtrate was cooled slowly to RT, upon which crystallization occurred and the mixture was allowed to stand at RT overnight. The filtrate was cooled to 0° C., and the solid xinafoate salt was isolated by vacuum filtration. The solid xinafoate salt was washed with isopropanol then ether and dried under high vacuum at 60° C. to give 36.8 g (81%) of a white solid.

Polymorph Form 1: Method 2:

To a 500 mL three necked round bottom flask, equipped with a nitrogen inlet and reflux condenser was added compound (5A) (30 g, 50.89 mmol, 1 eq) of Scheme 2, Example 2 and 1-hydroxy-2-napthoic acid (10.5 9, 55.80 mmol, 1.1 eq). To this flask was then added toluene (154 mL) and methanol (103 mL) and the resulting slurry was heated to ca. 62° C. at which time the contents became homogeneous. After stirring for 15 min, the contents were atmospherically distilled to 210 mL then cooled to ca 50° C. and then seeded with Form 1 crystals (3 g in 10 mL toluene, 10% by weight) causing the product salt to crystallize forming a slurry. After stirring this slurry for 30 min at 50° C., the contents were cooled to ca 10° C. at which time toluene (90 mL) was added and the slurry was vacuum distilled to ca 210 mL. A second addition of toluene (90 mL) was performed and the contents were stirred for 20 min at ca 20° C. The resulting solids were collected using an agitated dryer under vacuum and the wet cake was washed with toluene (60 mL). These solids were dried using the following protocol: (a) $T_j$=50° C., pressure=0.1 bar, no agitation, time=3 h; (b) $T_j$=80° C., pressure=0.1 bar, 20 rpm, time=12 h; (c) $T_j$=80° C., pressure=0.1 bar, 60 rpm, time=12 h. A total of 35 g (81%) of compound (6A) of Scheme 2, Example 2, was recovered as a solid.

$^1$H NMR (spectrum indicates rotomers, only chemical shift is reported, not integration or peak multiplicity; 400 MHz, $d_6$-DMSO) δ 9,86, 9.62, 8.55-8.41, 8.14, 8.03, 7.70, 7.45-7.37, 6.90, 5.46, 4.69, 4,57, 4.33, 4.15, 4.08, 3.99, 3.83, 2.39, 2.26, 2.16, 1.56, 1.44, 1.22, 0.82, 0.69

Polymorph Form 1 Method 3: A solution of Compound A (5.0 g, 0.00848 mol) in MeOH (75 ml) as heated to 50° C., filtered and rinsed with MeOH (10 ml). A solution of xinafoic acid (1.76 g, 0.00933 mol) in MeOH (35 ml) was heated to 50° C. and filtered into the Compound A solution. The mixture was heated to reflux for about 10 minutes, distilled atmospherically to about 50 ml, cooled to 0° C. over about 1 hour and agitated for about 30 minutes. The mixture was filtered, washed with chilled MeOH (20 ml) and dried at room temperature under vacuum for about 12 hours to give off-white solid 5.63 g (85.4%).

Polymorph Form 2; To a solution of Compound A (34.4 g, 0.0583 mol) dissolved in hot $CH_3OH$ (800 ml) was carefully added portionwise xinafoic acid (10.98 g, 0.0583 mol) while continuing to heat the $CH_3OH$ solution. Water (6 ml) was added. The reaction mixture was heated to near boiling to dissolve all solids, then filtered. The filtrate was cooled slowly to RT, upon which crystallization occurred and the mixture was allowed to stand at RT overnight. The filtrate was cooled to 0° C., and the solid xinafoate salt was isolated by vacuum filtration. The solid xinafoate salt was washed with isopropanol then ether and dried under high vacuum at 60° C. to give 36.8 g (81%) of a white solid Dihydrate Form 1: The addition of water during xinafoate salt formation is necessary to obtain the crystalline form. Dihydrate Form 1 was prepared by suspending Form 1 (504.83 mg, 0.65 mmol) in a mixture of water (0.9 mL) and methanol (3.1 mL). The suspension was stirred for 21 hours. Solids were isolated by centrifugation of the suspension then decanting off the supernatant. Solids were dried under vacuum at room temperature.

Polymorph Form a Form 3 was prepared by combining a mixture of the free base, Compound A (3.0 g, 5.1 mmol), and xinafoic acid (0.96 g, 5.1 mmol) in 2-propanol (90 mL). The mixture was heated to reflux and more 2-propanol (30 mL) was added. The mixture was held at reflux for 1 hour then cooled to room temperature. The mixture was filtered and solids were washed with 2-propanol (6 mL) then dried under vacuum to yield 3.24 g of product.

Powder X-Ray Diffraction Sample Preparation

Forms 1, 2, 3, and Dihydrate of Form 1 of the xinafoate salt were analyzed as a dry powder for powder x-ray diffraction ("PXRD") analyses. Form 1 was micronized in a jet mill before PXRD analysis using the following procedure.

Micronization by jet milling

The particle size distribution of the micronized powder is controlled by adjusting the jet pressure and the feed rate into the jet mill. The particles are fed at a rate of 1 g/min into the milling chamber of the MC ONE JETMILL (Jetpharma Group, South Plainfield, N.J.) through a venturi system by pressurized nitrogen. The pressure drop across the venturi is set at 5 bar. The particles are accelerated in a spiral movement inside the milling chamber by four nozzles placed around the periphery of the milling chamber. The pressure drop across the nozzles is set at 4 bar. The micronizing effect takes place by the collision between the slower incoming particles and those already accelerated in the spiral stream. Centrifugal forces retain the larger particles at the periphery of the milling chamber, while the smaller particles exit with the exhaust gas from the center of the chamber by means of a static classifier and are recovered in a collecting container just beneath the jet mill.

The samples were analyzed with minimal preparation to prevent any form changes. The samples were lightly rubbed to insure that particles were not agglomerated. No solvents, drying or other preparation steps were used for these analyses. The PXRD data can uniquely identify the hydrate and polymorphic forms.

Powder X-Ray Diffraction

X-Ray powder diffraction patterns of Forms 1 and 2 were collected on a Rigaku Miniflex diffractometer equipped with a CuKα radiation (λ=1.54056 Å) at 30 kv, 15 mA and a solid state detector (Rigaku MSC, The Woodlands, Tex.). A continuous scan was recorded for all samples with a step size of 0.02° 2θ and a scanning rate of 2°/min.

X-ray powder diffraction patterns of Dihydrate Form 1 were collected on Bruker D8 Diffractometer with $CuK_{\alpha 1}$ source (λ=1.5406 Å) at 40 kV and 40 mA. A continuous scan was recorded with a step size of 0.032° 2θ and a step time of 0.5 second.

X-Ray powder diffraction patterns of Form 3 were collected on a Kratos XRD 6000. Samples were prepared by lightly packing material into the sample holder and gently smoothing to produce a flat sample surface. Samples were analyzed from 2 to 40 degrees 2 Theta with a step size of 0.02 degrees and step durations of 0.6 seconds. Data analysis was conducted using Basic Process software, version 2.6, supplied by Kratos. The data was smoothed using the automatic smoothing process in the software.

Using the methods and equipment described above, Form 1, Form 2 and Form 3 polymorph xinafoate salt and the Dihydrate Form of Compound A were subjected to PXRD analysis. PXRD patterns were generated and are displayed in FIGS. 1-3 and 10. The intensity of the peaks (y-axis is in counts per second) is plotted vesus the 2θ angle (x-axis is in degrees 2θ). In addition, the data were plotted with detector counts normalized for the collection time per step versus the 2θ angle. Peak locations (on the 2θ X-axis) consistent with these profiles are displayed in Table 1. The locations of these PXRD peaks are characteristic of crystalline polymorphs of Forms 1, 2, 3 and the crystalline Dihydrate Form 1 of the compound of formula I.

TABLE 1

PXRD Peak Positions for Forms 1, 2, 3 and Dihydrate Form 1

| Form 1 | | Form 2 | | Dihydrate Form 1 | | Form 3 | |
| --- | --- | --- | --- | --- | --- | --- | --- |
| Peak Location (deg. 2θ) | Intensity (Cps) | Peak Location (deg. 2θ) | Intensity (Cps) | Peak Location (deg. 2θ) | Intensity (Cps) | Peak Location (deg. 2θ) | Intensity (Cps) |
| 5.6 | 2023 | 4.5 | 290 | 5.5 | 1208 | 4.6 | 5605 |
| 6.1 | 5570 | 6.9 | 239 | 7.2 | 1066 | 7.9 | 1225 |
| 6.4 | 156 | 9.0 | 374 | 8.2 | 86658 | 9.1 | 882 |
| 7.7 | 4978 | 9.4 | 625 | 11.6 | 620 | 12.1 | 1718 |
| 9.3 | 511 | 10.6 | 4176 | 12.8 | 328 | 13.0 | 217 |
| 9.7 | 270 | 11.6 | 319 | 13.7 | 866 | 13.7 | 1243 |

TABLE 1-continued

PXRD Peak Positions for Forms 1, 2, 3 and Dihydrate Form 1

| Form 1 | | Form 2 | | Dihydrate Form 1 | | Form 3 | |
|---|---|---|---|---|---|---|---|
| Peak Location (deg. 2θ) | Intensity (Cps) | Peak Location (deg. 2θ) | Intensity (Cps) | Peak Location (deg. 2θ) | Intensity (Cps) | Peak Location (deg. 2θ) | Intensity (Cps) |
| 10.3 | 973 | 13.6 | 6557 | 14.3 | 2078 | 15.2 | 383 |
| 12.2 | 129 | 14.9 | 135 | 14.7 | 948 | 15.8 | 792 |
| 13.0 | 3733 | 16.5 | 357 | 16.5 | 16206 | 16.5 | 1065 |
| 13.4 | 252 | 17.9 | 904 | 16.9 | 1402 | 17.8 | 198 |
| 14.2 | 450 | 18.8 | 906 | 17.4 | 612 | 18.3 | 172 |
| 15.3 | 235 | 19.1 | 2737 | 18.5 | 3106 | 18.9 | 1315 |
| 15.9 | 2434 | 20.2 | 679 | 19.1 | 1236 | 20.0 | 800 |
| 16.2 | 101 | 21.2 | 4129 | 19.9 | 654 | 21.0 | 295 |
| 16.6 | 296 | 22.7 | 301 | 20.6 | 2604 | 22.0 | 248 |
| 17.8 | 3180 | 23.2 | 171 | 21.6 | 430 | 23.9 | 368 |
| 18.4 | 595 | 23.9 | 733 | 22.0 | 790 | 24.3 | 352 |
| 18.9 | 486 | 24.6 | 151 | 23.4 | 458 | 24.9 | 302 |
| 19.4 | 160 | 26.0 | 400 | 24.1 | 814 | 25.7 | 985 |
| 20.1 | 301 | 26.6 | 520 | 24.9 | 3626 | 26.6 | 172 |
| 20.5 | 1355 | 27.2 | 262 | 25.9 | 642 | 27.4 | 243 |
| 21.1 | 409 | 28.1 | 543 | 26.8 | 838 | 27.8 | 347 |
| 21.8 | 754 | 29.7 | 274 | 27.8 | 782 | 28.8 | 220 |
| 22.1 | 583 | 30.8 | 221 | 28.8 | 604 | | |
| 22.9 | 795 | 31.5 | 204 | 31.8 | 502 | | |
| 23.3 | 231 | 32.3 | 66 | | | | |
| 23.9 | 399 | 33.1 | 175 | | | | |
| 24.4 | 185 | 33.9 | 138 | | | | |
| 25.5 | 120 | 34.7 | 188 | | | | |
| 26.1 | 602 | 36.2 | 163 | | | | |
| 26.8 | 321 | 37.1 | 182 | | | | |
| 27.3 | 214 | | | | | | |
| 27.8 | 414 | | | | | | |
| 28.1 | 171 | | | | | | |
| 30.4 | 113 | | | | | | |
| 30.8 | 375 | | | | | | |
| 31.6 | 103 | | | | | | |
| 33.4 | 422 | | | | | | |
| 34.6 | 1244 | | | | | | |
| 36.2 | 228 | | | | | | |
| 36.6 | 223 | | | | | | |
| 36.9 | 146 | | | | | | |
| 38.1 | 219 | | | | | | |
| 39.6 | 408 | | | | | | |

Starting with PXRD peak locations as displayed in Table 1, the most characteristic peak locations of each polymorph or hydrate can be selected and grouped by relative intensity to conveniently distinguish the crystalline structure from others.

Such a selection of unique peaks is displayed in Table 2. Thus, for example, the crystalline structure of Form 1 of the compound of formula I may be identified by the Peak Location Group No. 1, consisting of 4 characteristic PXRD peak locations. Alternatively, the crystalline structure of Form 1 of the compound of formula I may be identified by the Peak Location Group No. 2, consisting of the 4 characteristic PXRD peak locations of Group No. 1 and an additional 4 peak locations. Alternatively, the Form 1 crystalline structure of the compound of formula I may be identified by the Peak Location Group No. 3, consisting of the 8 characteristic PXRD peak locations of Group No. 2 and an additional 4 peak locations. This scheme is applied to each of the four polymorphic forms to identify and distinguish each form from the other.

TABLE 2

Characteristic PXRD Peak Locations for Forms 1, 2, 3 and Dihydrate of Form 1 of Formula I

| Peak Location Group No | Peak Locations (degrees 2θ) | | | |
|---|---|---|---|---|
| | Polymorph Form 1 | Dihydrate Form 1 | Polymorph Form 2 | Polymorph Form 3 |
| 1 | 6.1 | 8.2 | 10.6 | 4.6 |
| | 7.7 | 16.5 | 13.6 | 7.9 |
| | 13.0 | 18.5 | 19.1 | 12.1 |
| | 15.9 | 24.9 | 21.2 | 18.9 |
| 2 | 5.6 | 5.5 | 10.6 | 4.6 |
| | 6.1 | 8.2 | 13.6 | 7.9 |
| | 7.7 | 14.3 | 17.9 | 9.1 |
| | 13.0 | 16.5 | 18.8 | 12.1 |
| | 15.9 | 16.9 | 19.1 | 13.7 |
| | 17.8 | 18.5 | 20.2 | 15.8 |
| | 18.4 | 20.6 | 21.2 | 16.5 |
| | 26.1 | 24.9 | 23.9 | 18.9 |
| 3 | 5.6 | 5.5 | 9.4 | 4.6 |
| | 6.1 | 7.2 | 10.6 | 7.9 |

TABLE 2-continued

Characteristic PXRD Peak Locations for Forms 1, 2, 3 and Dihydrate of Form 1 of Formula I

| Peak Location Group No | Peak Locations (degrees 2θ) | | | |
|---|---|---|---|---|
| | Polymorph Form 1 | Dihydrate Form 1 | Polymorph Form 2 | Polymorph Form 3 |
| | 7.7 | 8.2 | 13.6 | 9.1 |
| | 9.2 | 14.3 | 17.9 | 12.1 |
| | 13.0 | 14.7 | 18.8 | 13.7 |
| | 14.2 | 16.5 | 19.1 | 15.8 |
| | 15.9 | 16.9 | 20.2 | 16.5 |
| | 17.8 | 18.5 | 21.2 | 18.9 |
| | 18.4 | 20.6 | 23.9 | 20.0 |
| | 20.5 | 24.1 | 26.0 | 23.9 |
| | 22.9 | 24.9 | 26.6 | 24.3 |
| | 26.1 | 26.8 | 28.1 | 25.7 |

Those skilled in the art will recognize that the measurements of the PXRD peak locations for a given crystalline form of the same compound will vary within a margin of error. Such variation can be introduced by differences in sample preparation, instrumentation, or analytical technique, among other factors. Measurements of individual peak locations can vary to a small degree, but an entire peak profile can vary by a greater degree, due to variations in density of packed samples, for example, Polymorph Purity Preferably, the crystalline polymorph Forms 1, 2, 3 and Dihydrate Form 1 of the compound of formula I are substantially free of chemical impurities (e.g., by-products generated during the preparation of the polymorphs) and of other polymorphic crystalline forms. "Substantially free" of chemical impurities for the purposes of this invention means less than or equal to about 5% w/w of chemical impurities, preferably, less than or equal to about 3% w/w of chemical impurities, more preferably, less than or equal to about 2% w/w of chemical impurities, and even more preferably, less than or equal to about 1% w/w of chemical impurities. The term "purified" or "in purified form" for a polymorph refers to the physical state of said polymorph after being obtained from a purification process or processes described herein or well known to the skilled artisan, in sufficient purity to be characterizable by standard analytical techniques described herein or well known to the skilled artisan. Purified forms of the crystalline polymorph Forms 1, 2 and 3 and the Dihydrate Form 1 of the compound of formula I are substantially free of chemical impurities.

Differential Scanning Calorimetry

The DSC instrument used to test the polymorph Forms 1 and 2 samples was a TA Instruments® model 2920 (manufactured in 2001), which came equipped with a refrigerated cooling system. The DSC cell/sample chamber was purged with 40 ml/min of ultra-high purity nitrogen gas. The instrument was calibrated with high purity indium. The accuracy of the measured sample temperature with this method is within about ±1° C., and the heat of fusion can be measured within a relative error of about ±5%. The sample was placed into a standard aluminum DSC pan with a lid containing two pin holes to allow for pressure release. About 2 mg of sample powder was placed into the bottom of the pan and lightly tapped down to make contact with the pan. The weight of the sample was measured accurately and recorded to a hundredth of a milligram. The instrument used an empty reference pan. The DSC analysis was conducted at 10° C./min heating rate.

The DSC instrument used to test the Dihydrate Form 1 and polymorph Form 3 samples was a Q100 TAInstruments® Again, samples were sealed in the hermetic aluminum pans and two pinholes were punched in the lids of the sample pans. Analysis was conducted under a nitrogen purge with a heating rate of 10° C. per minute.

The heat flow, which was normalized by a sample weight, was plotted versus the measured sample temperature. The data were repored in units of watts/gram ("W/g"). The plot was made with the endothermic peaks pointing down. The endothermic melt peak was evaluated for extrapolated onset and end (outset) temperatures, peak temperature, and heat of fusion in this analysis.

Figure 6:
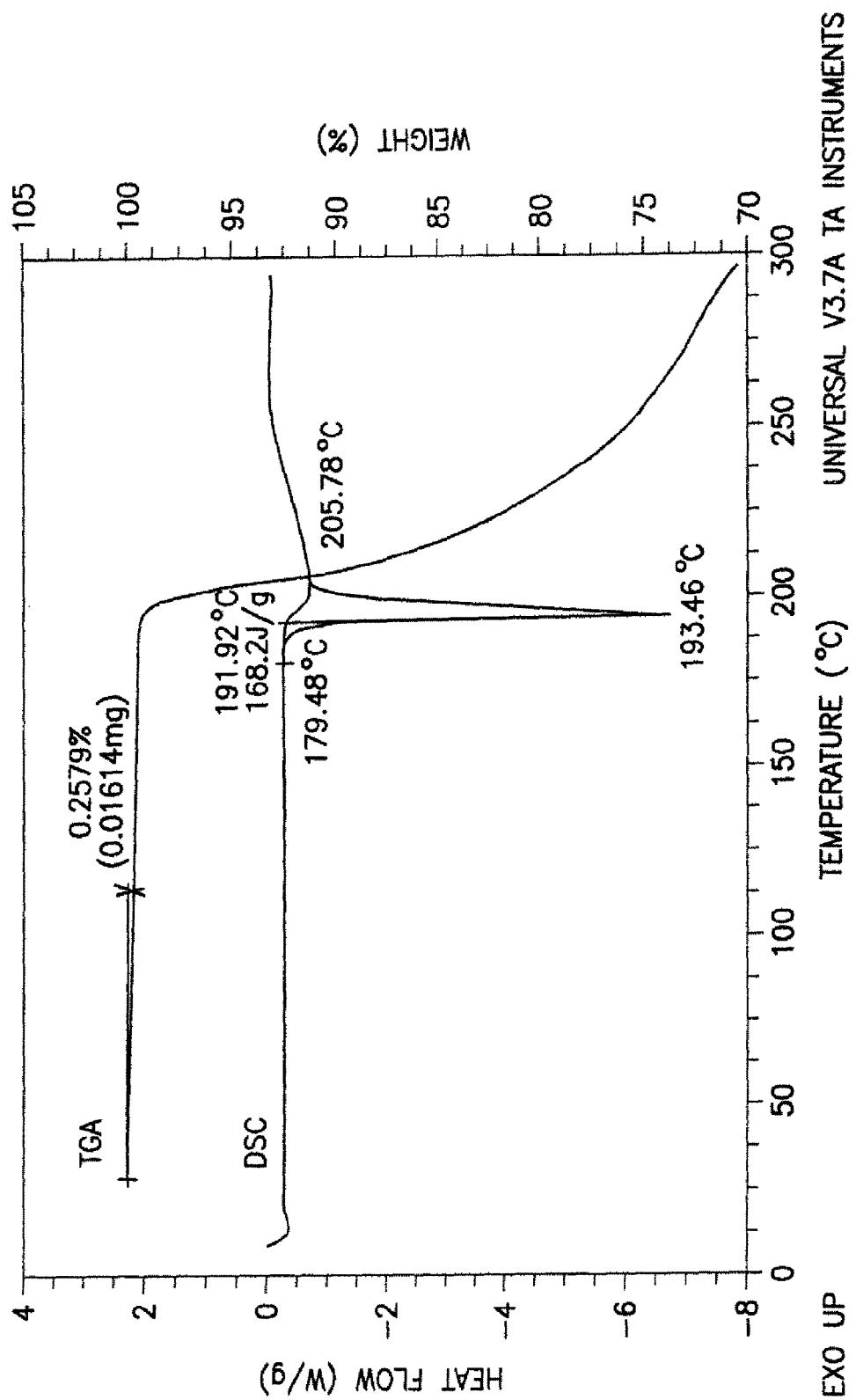
FIG. 6 is a plot of the thermal analysis of Form 1 of the compound of formula I generated by Differential Scanning Calorimetry (DSC).

A DSC profile for Form 1 of formula I is displayed in FIG. 6. For Form 1 of the compound of formula I, a single endotherm was observed with onset temperature of 192° C. and peak temperature of 193° C.

Figure 7:
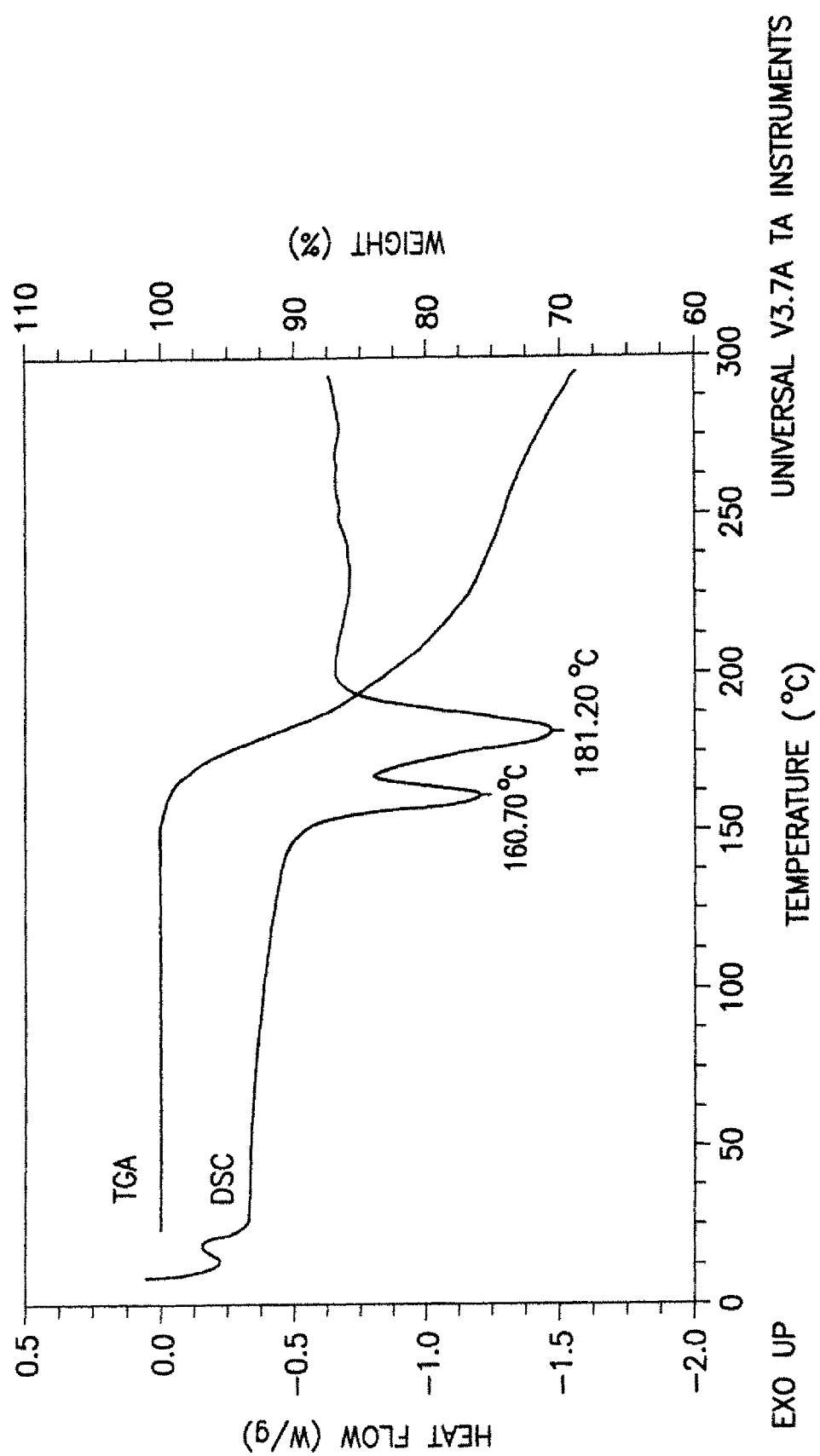
FIG. 7 is a plot of the thermal analysis of Form 2 of the compound of formula I generated by Differential Scanning Calorimetry (DSC).

A DSC profile for Form 2 of formula I is displayed in FIG. 7. For Form 2 of the compound of formula I, two overlapped endotherms were observed with onset temperature of 152° C. and peak temperatures of 161° C. and 181°C.

Figure 8:
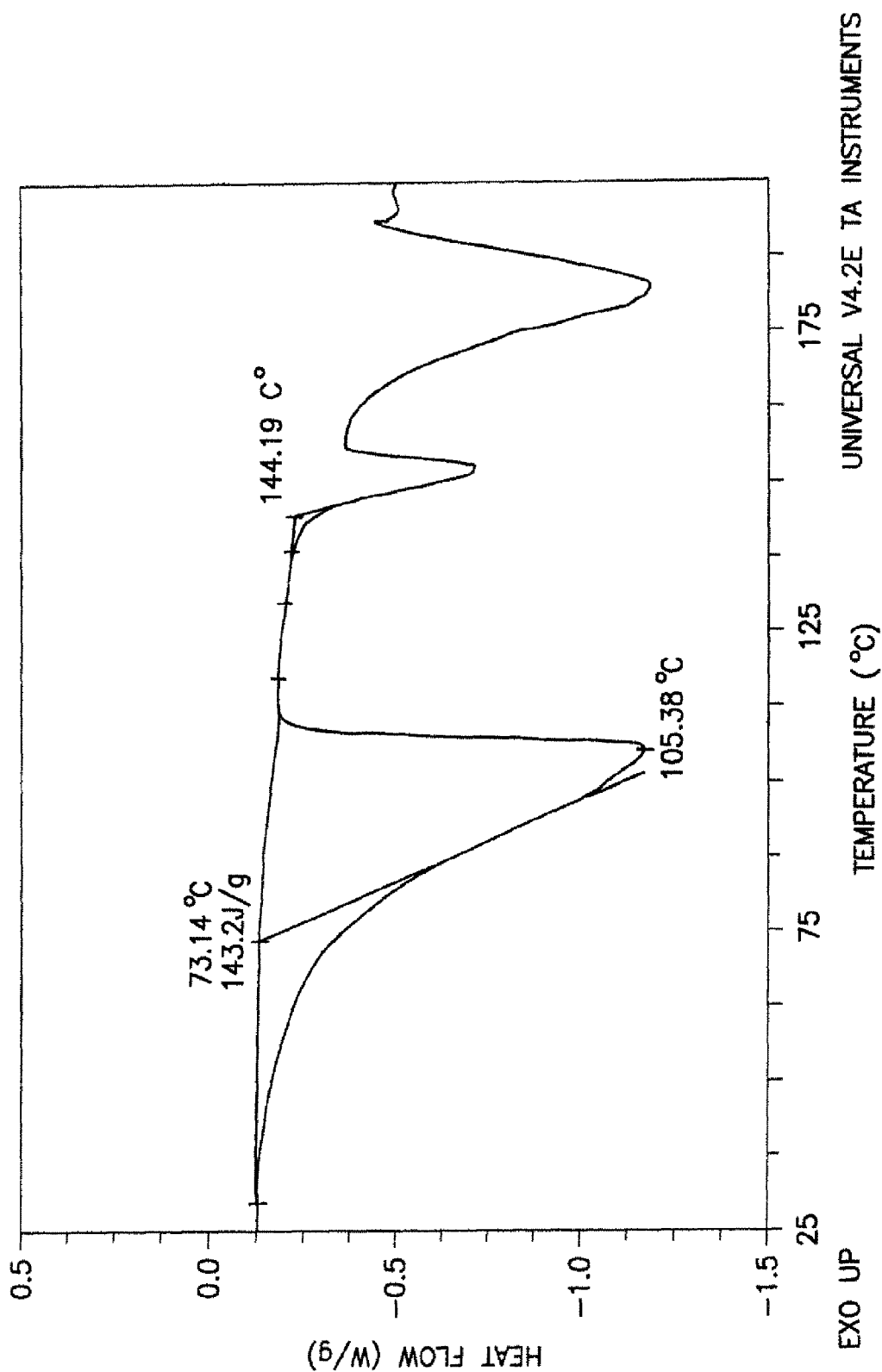
FIG. 8 is a plot of the thermal analysis of Dihydrate Form 1 of the compound of formula I generated by Differential Scanning Calorimetry (DSC).
Figure 9:
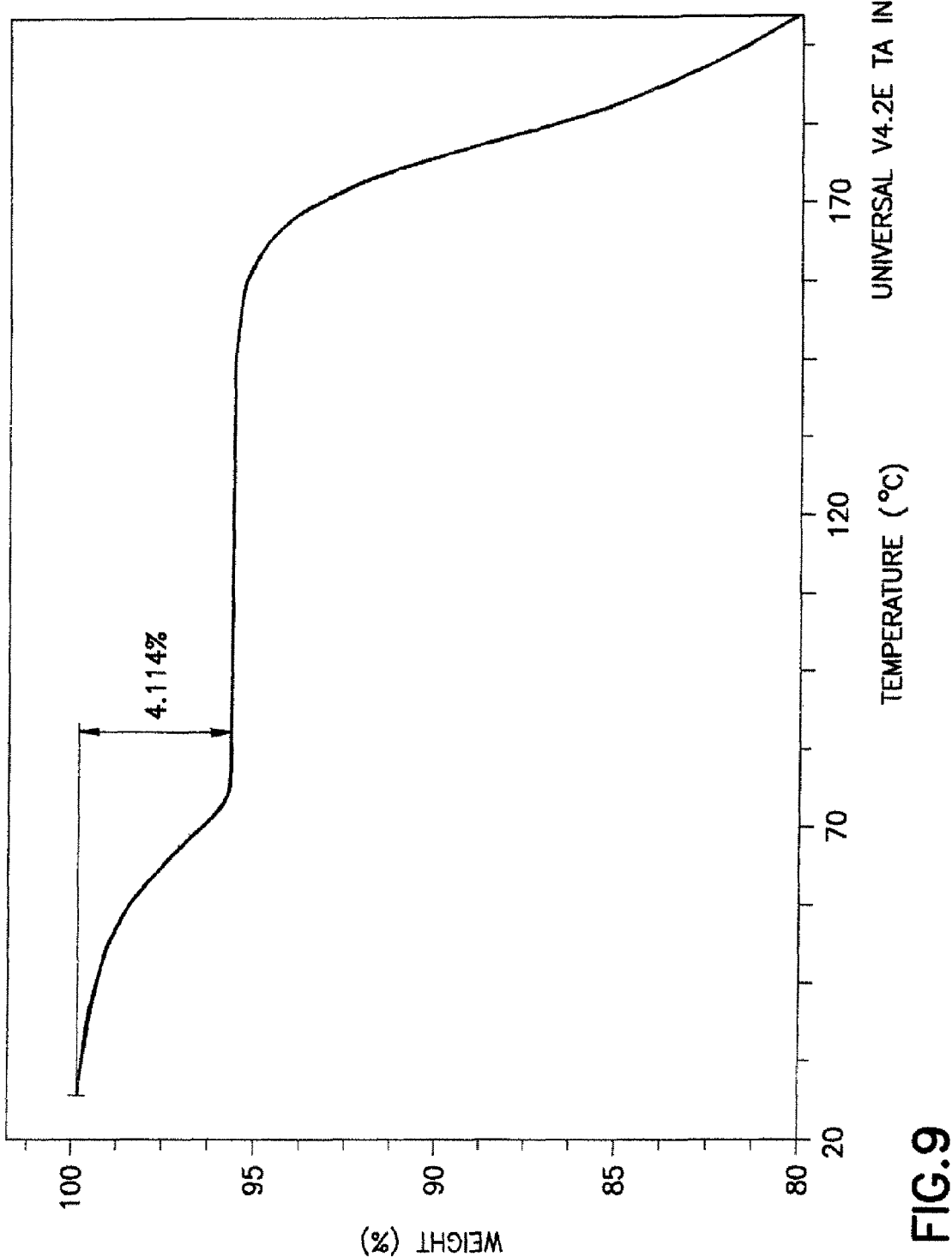
FIG. 9 is a plot of the thermal gravimetric analysis of Dihydrate Form 1 of the compound of formula I generated by Thermogravimetric Analysis (TGA).
Figure 10:
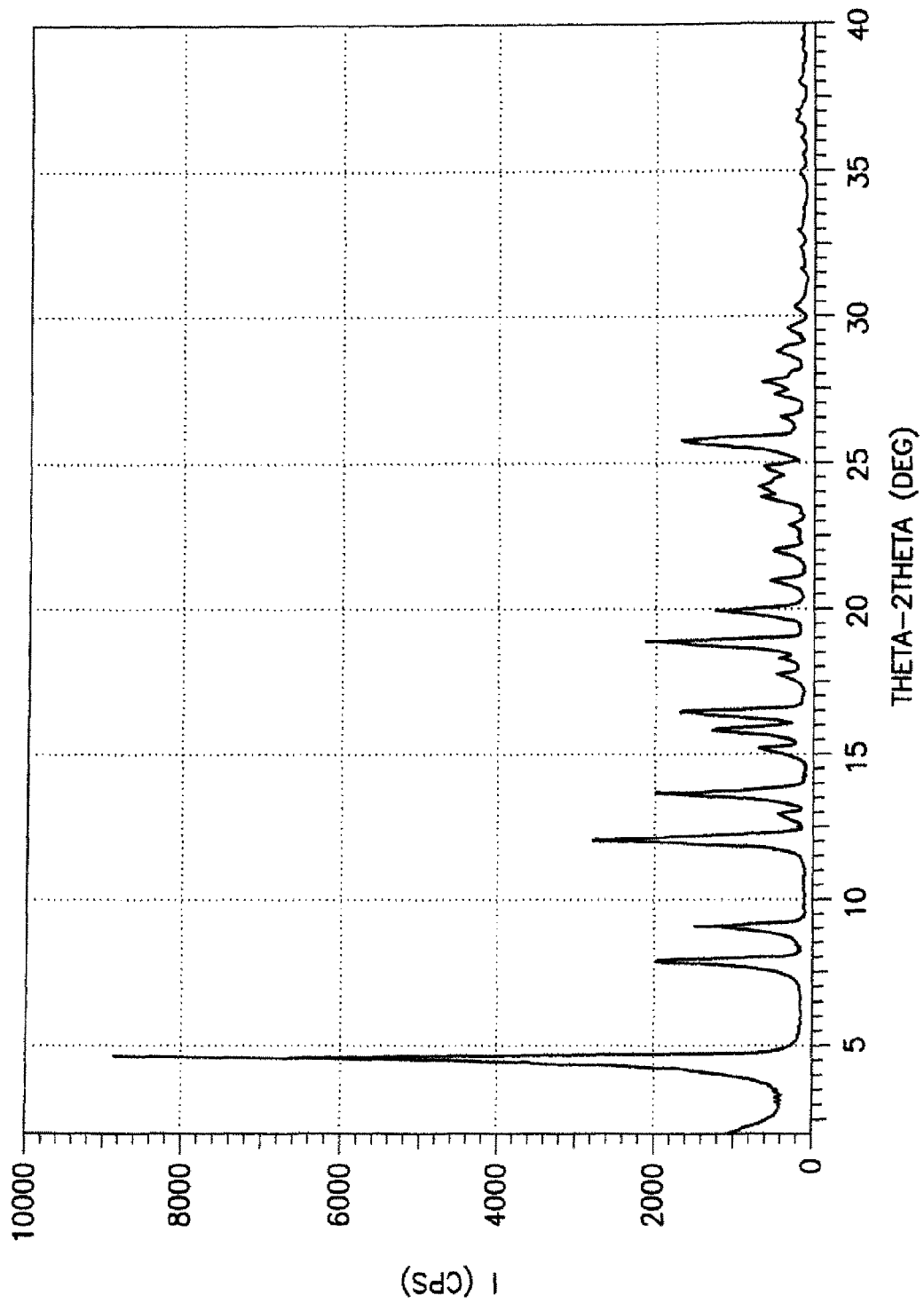
FIG. 10 is a graph of a PXRD pattern of Form 3 of the compound of formula I, generated using an X-ray diffractometer. The graph plots the intensity of the peaks as defined by counts per second versus the diffraction angle 2θ in degrees.

A DSC profile for Dihydrate Form 1 of formula I is displayed in FIG. 8. For Dihydrate Form 1 of the compound of formula I, at 10° C./min, the Dihydrate Form 1 undergoes dehydration and transforms to a room temperature metastable anhydrous form. This event is reflected on the DSC thermogram (FIG. 8) as a broad endotherm with onset temperature at 73° C. and the heat of 143 J/g. The amount of the hydrate water lost during heating accounts for 4.1% of the total weight, which is shown as a step-like weight loss in the TGA data (FIG. 9), indicating Dihydrate stoichiometry. The room temperature metastable form undergoes melting with onset temperature at 144° C. The heat of fusion cannot be determined due to the onset of decomposition, which corresponds to the weight loss after 150° C. in TGA data (FIG. 9), prior to the completion of the melting event.

Figure 11:
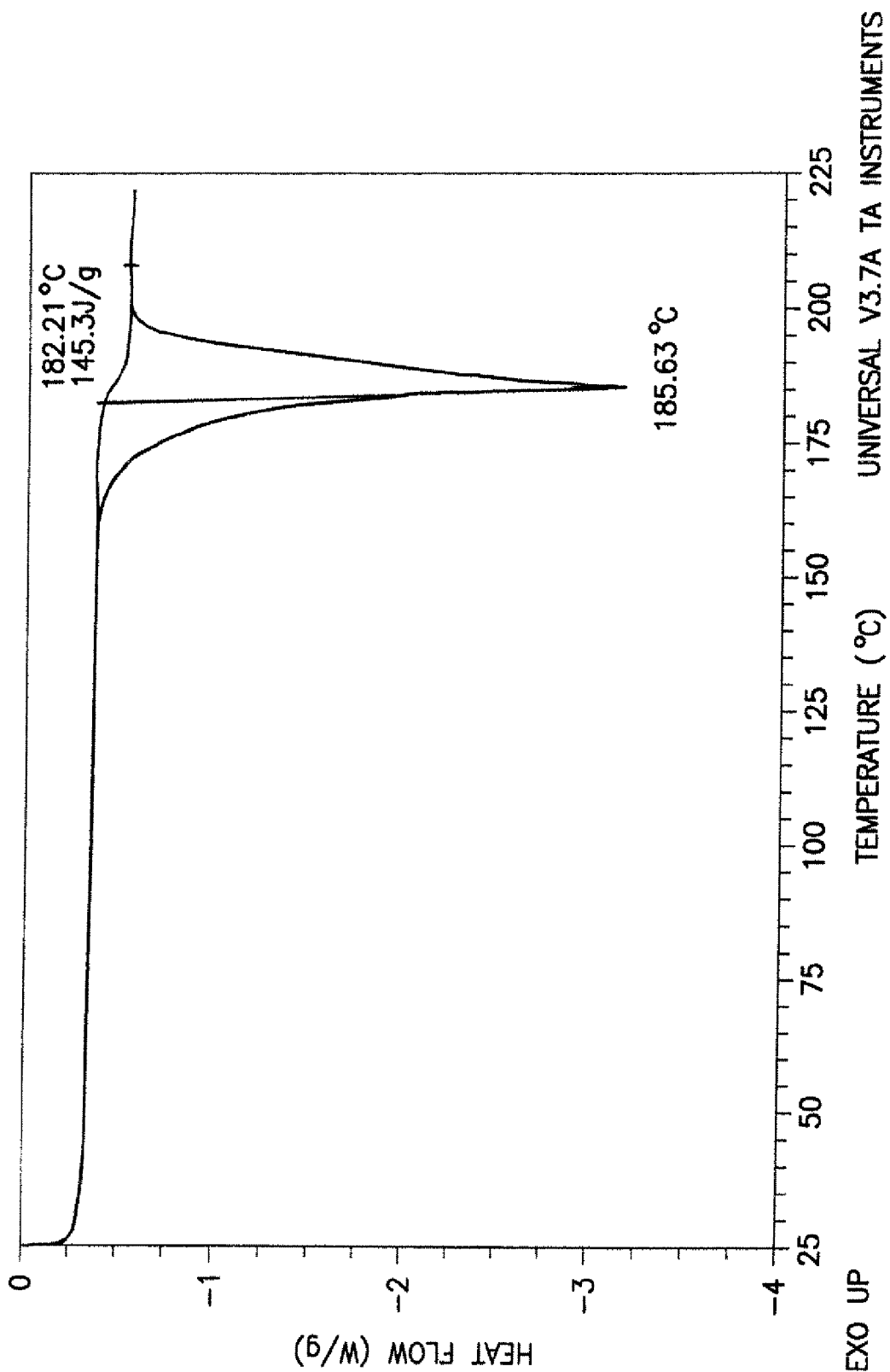
FIG. 11 is a plot of the thermal analysis of Form 3 of the compound of formula I generated by Differential Scanning Calorimetry (DSC).

A DSC profile for Form 3 of formula I is displayed in FIG. 11. For Form 3 of the compound of formula I, a single endotherm with an onset temperature of 182° C. and a peak temperature of 186° C. was observed.

The premise for treatment by inhalation is to deliver the drug directly to the site of action (the lungs) with minimal systemic side effects. Therefore, an inhaled compound should exhibit a pharmacokinetic profile with low blood concentration (AUC) due to low oral bioavailability and/or high clearance when given by inhalation or oral dosing routes. It is important that oral AUC be low in order to minimize the effect of any swallowed drug during inhalation. Often times, low AUC levels are difficult to measure. Therefore, reproducible AUC data is preferred.

Assay Protocol for Allergic Brown-Norway Rats:

Inbred male BN rats weighing 150 to 200 g were obtained from Charles River Laboratory (Wilmington, Mass.). Prior to use, the animals were allowed food and water ad libitum. The test compounds were administered 5 h prior to antigen challenge either by oral or inhalational route, as detailed in the "delivery of test compounds" section.

Sensitization and Antigen Bronchoprovocation

The animals were divided into two main groups viz. an alum group and an antigen group. In the antigen group, animals were sensitized by an intra-peritoneal (i.p.) injection of 1 ml alum-precipitated antigen containing 20 μg of ovalbumin (OVA, grade III; Sigma chemical Co., St Louis, Mo.) and 8 mg of $Al(OH)_3$ suspended in 0.9% saline vehicle. A booster injection of this alum-OVA mixture was given again 7 days later. Animals belonging to the alum group received injections containing alum only. Seven days after the second injection, animals were exposed to aerosolized antigen bronchoprovocation which was performed by placing the rats in an enclosed plexiglass chamber (21 liters) and exposing the rats to aerosolized OVA (1%) for 30 min. The aerosolized OVA was produced by an ultrasonic nebulizer (DeVilbiss, Somerset, Pa., USA; Model Ultra-Neb 99) at a flow rate of approximately 8 liters/min. Twenty four hours after aerosolized OVA challenge, the animals were euthanized with an overdose of pentobarbital sodium. The trachea was exteriorized and intubated, and the lungs were ravaged with two aliquots of 3 ml of physiological saline. The bronchoalveolar lavage fluid (BALF) thus collected was subjected to cell enumeration. Ten microliter of the BALF was utilized to manually enumerate the total white cells using a hemocytometer. One hundred microliter of BALF was used to prepare cytocentrifuge which was stained with Hema3™ staining system (Fisher Scientific, Springfield, N.J.) to identify and enumerate differential white blood cells such as eosinophils, neutrophits, mononuclear cells and epithelial cells. A total of 200 cells were enumerated from each cytocentrifuge. The ability of the compound to inhibit recruitment of inflammatory cells into the airways is reported.

Delivery of Test Compounds:

Oral administration: the compounds were dissolved in 0.4% methylcellulose and delivered to animals orally @ 3 ml/kg. An equivalent volume of 0.4% methylcellulose was given to both negative (alum group) and positive (antigen) control groups.

Intra-tracheal administration: the appropriate dose of the compound was mixed with lactose powder to achieve a final amount of 3 mg, which was delivered intra-tracheally to anesthetized animals using a fine-tipped microsprayer. Animals were held in an upright position for 3-4 min and were allowed to recover from anesthesia before returning to their cages.

Using the above test procedures, the following results were obtained: tartrate salt: 52% inhibition of inflammatory cells at 0.02 mpk (intra-tracheal dosing) xinafoate salt: 69% inhibition of inflammatory cells at 0.02 mpk (intra-tracheal dosing)

Assay Protocol for Monkey PK Assay:

Two fasted monkeys were dosed orally at 3 mpk with the test compound in 0.4% HPMC vehicle. The dose volume was 2 ml/kg dose. Plasma was collected at 0.5, 1, 2, 4, 8, and 24 hr. Blood samples were collected with heparin, and the plasma was stored with EDTA. Blood samples for each individual animal were characterized by MS/MS analysis.

Using the above test procedure, the following results were obtained:
tartrate salt: monkey AUC=30 ng.h/mL at 10 mpk po
xinafoate salt: monkey AUC=0 ng.h/mL at 10 mpk po
Assay Protocol for Rat PK Assay:

Two fasted Sprague Dawley rats were dosed orally at 10 mpk with compound in 0.4% HPMC vehicle. The dose volume was 5 ml/kg dose. Plasma was collected at 0.5, 1, 2, 3, 4, and 6 hr. Blood samples were collected with heparin, and the plasma was stored with EDTA. The two blood samples at each timepoint were pooled for MS/MS analysis
tartrate salt: AUC=0 to 1350 ng.h/mL at 30 mpk po (variable)
xinafoate salt: AUC=350 ng.h/mL at 30 mpk po
Assay Protocol for Lung Function Assay:

Lung function was measured using a forced expiratory maneuvers technique. In this procedure, the rats were anesthetized and a tracheal catheter was inserted. The rats were placed inside a whole body plethysmograph that contained a breathing valve capable of separating inflations and deflations of the lungs. The lungs were then subject to forced inflation of the lungs to total lung capacity followed by rapid deflation to residual volume. Measurements of forced vital capacity and peak expiratory flow were used to measure the effects of antigen challenge and assess the inhibitory effects of the compound of formula I. The drug was admixed with lactose for intratracheal delivery and given directly into the trachea with a fine microsprayer 5 hr before the antigen challenge. Orally delivered compound was given in 0.4% methylcellulose vehicle 5 hr before the antigen challenge. Control animals received intratracheal lactose or methylcellulose, respectively. The antigen challenge consisted of aerosolized exposure for 30 min to 1% ovalbumin. Forced expiratory lung functions were measured 24 hr after the antigen (ovalbumin) exposure.

The compound of formula I exhibits 54% inhibition of forced vital capacity (FVC) at 0.02 mpk it (intra-tracheal) and 31% inhibition of FVC at 3 mpk po.

Pharmaceutical Compositions

For preparing pharmaceutical compositions from the polymorphs described by this invention, inert, pharmaceutically acceptable carriers can be either solid or liquid. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton. Pa.

Liquid form preparations include solutions, suspensions and emulsions for intranasal administration.

Aerosol preparations suitable for inhalation may include solutions and solids in powder form, which may be in combination with a pharmaceutically acceptable carrier, such as an inert compressed gas, e.g. nitrogen.

Dosages

The quantity of active compound in a unit dose of preparation may be varied or adjusted from about 0.01 µg to about 100 mg, preferably from about 0.01 µg to about 75 mg, more preferably from about 0.01 µg to about 50 mg, and most preferably from about 0.01 µg to about 25 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for inhalation can range from about 0.04 µg /day to about 400 mg/day, in one to four divided doses.

Other than as shown in the operating examples or as otherwise indicated, all numbers used in the specification and claims expressing quantities of ingredients, reaction conditions, and so forth, are understood as being modified in all instances by the term "about." The above description is not intended to detail all modifications and variations of the invention. It will be appreciated by those skilled in the art that changes can be made to the embodiments described above without departing from the inventive concept. It is understood, therefore, that the invention is not limited to the particular embodiments described above, but is intended to cover modifications that are within the spirit and scope of the invention, as defined by the language of the following claims.

What is claimed is:
1. The compound having the structural formula

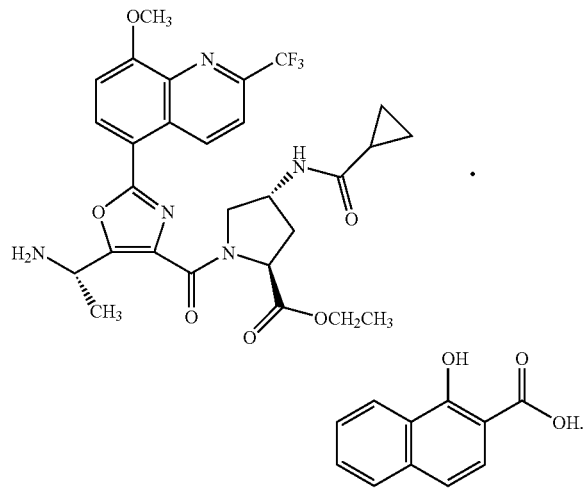

2. A method of treating upper or lower obstructive diseases of the airways in a patient in need of such treatment comprising administering to said patient by inhalation an effective amount of the compound of claim 1.

3. The method of claim 2 wherein the disease treated is asthma or chronic obstructive pulmonary disease.

4. A method of treating upper or lower obstructive diseases of the airways in a patient in need of such treatment comprising administering to said patient by inhalation an effective amount of a combination of the compound of claim 1 and at least one additional agent useful for treating upper or lower obstructive diseases of the airway.

5. The method of claim 4 wherein the disease treated is asthma or chronic obstructive pulmonary disease.

6. The method of claim 4 wherein the additional agent is selected from the group consisting of beta-agonists, muscarinic antagonists and corticosteroids.

7. An inhalable pharmaceutical composition comprising an effective amount of the compound of claim 1.

8. An inhalable pharmaceutical composition comprising an effective amount of a combination of the compound of claim 1 and at least and at least one additional agent useful for treating upper or lower obstructive diseases of the airway.

9. A composition of claim 8 wherein the additional agents are selected from the group consisting of beta-agonists: muscarinic antagonists and corticosteroids.

10. A crystalline polymorph of a compound of the formula:

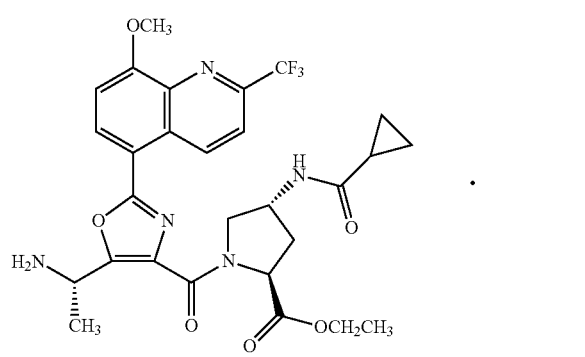

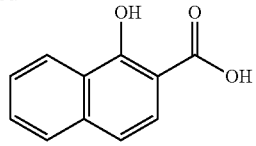

wherein, said polymorph is selected from the group consisting of:
Form 1 that exhibits a powder x-ray diffraction pattern substantially the same as the pattern shown in FIG. 1;
Form 2 that exhibits a powder x-ray diffraction pattern substantially the same as the pattern shown in FIG. 2; and
Dihydrate Form 1: that exhibits a powder x-ray diffraction pattern substantially the same as the pattern shown in FIG. 3;
Form 3 that exhibits a powder x-ray diffraction pattern substantially the same as the pattern shown in FIG. 10.

11. A crystalline polymorph Form 1 of the compound of claim 10 that exhibits a powder x-ray diffraction pattern having characteristic peak locations of 6.1, 7.7, 13.0 and 15.9 degrees 2θ.

12. The crystalline polymorph of claim 11 that exhibits a powder x-ray diffraction pattern having characteristic peak locations of 5.6, 6.1, 7.7, 13.0, 15.9, 17.8, 18.4 and 26.1 degrees 2θ.

13. The crystalline polymorph of claim 11 that exhibits a powder x-ray diffraction pattern having characteristic peak locations of 5.6, 6.1, 7.7, 9.2, 13.0, 14.2, 15.9, 17.8, 18.4, 20.5, 22.9 and 26.1 degrees 2θ.

14. The crystalline polymorph Form 1 of claim 10.

15. A crystalline polymorph Form 2 of the compound of claim 10 that exhibits a powder x-ray diffraction pattern having characteristic peak locations of 10.6, 13.6, 19.1 and 21.2 degrees 2θ.

16. The crystalline polymorph of claim 15 that exhibits a powder x-ray diffraction pattern having characteristic peak locations of 10.6, 13.6, 17.9, 18.8, 19.1, 20.2, 21.2 and 23.9 degrees 2θ.

17. The crystalline polymorph of claim 15 that exhibits a powder x-ray diffraction pattern having characteristic peak locations of 9.4, 10.6, 13.6, 17.9, 18.8, 19.1, 20.2, 21.2, 23.9, 26.0, 26.6 and 28.1 degrees 2θ.

18. The crystalline polymorph Form 2 of claim 10.

19. A crystalline Dihydrate Form 1 of the compound of claim 10 that exhibits a powder x-ray diffraction pattern having characteristic peak locations of 8.2, 16.5, 18.5 and 24.9 degrees 2θ.

20. The crystalline dihydrate of claim 19 that exhibits a powder x-ray diffraction pattern having characteristic peak locations of 5.5, 8.2, 14.3, 16.5, 16.9, 18.5, 20.6, and 24.9 degrees 2θ.

21. The crystalline dihydrate of claim 19 that exhibits a powder x-ray diffraction pattern having characteristic peak locations of 5.5, 7.2, 8.2, 14.3, 14.7, 16.5, 16.9, 18.5, 20.6, 24.1, 24.9 and 26.8 degrees 2θ.

22. The crystalline Dihydrate Form 1 of claim 10.

23. A crystalline polymorph Form 3 of the compound of claim 10 that exhibits a powder x-ray diffraction pattern having characteristic peak locations of 4.6, 7.9, 12. 1, and 18.9 degrees 2θ.

24. The crystalline polymorph of claim 23 that exhibits a powder x-ray diffraction pattern having characteristic peak locations of 4.6, 7.9, 9.1, 12.1, 13.7, 15.8, 16.5, and 18.9 degrees 2θ.

25. The crystalline polymorph of claim 23 that exhibits a powder x-ray diffraction pattern having characteristic peak locations of 4.6, 7.9, 9.1, 12.1, 13.7, 15.8, 16.5, 18.9, 20.0, 23.9, 24.3 and 25.7 degrees 2θ.

26. The crystalline polymorph Form 3 of claim 10.

27. A process for preparing the polymorph Form 1 of claim 10 from

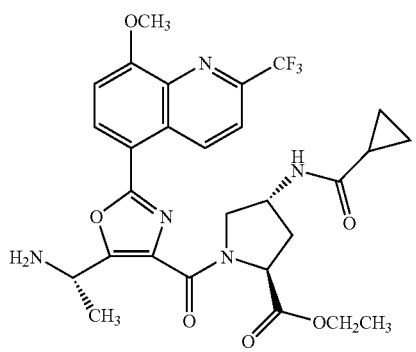

Compound A comprising the steps of:
a) dissolving compound of Compound A, in hot ethanol and adding xinafoic acid while continuing to heat the mixture;
b) adding additional ethanol and water, and heating the mixture to near boiling;
c) filtering the hot mixture, then cooling slowly to room temperature and allowing the mixture to stand at room temperature overnight until Form 1 crystals precipitate; and
d) cooling the filtrate to 0° C. and filtering the Form 1 crystals.

28. A process for preparing the polymorph Form 1 of claim 10 from

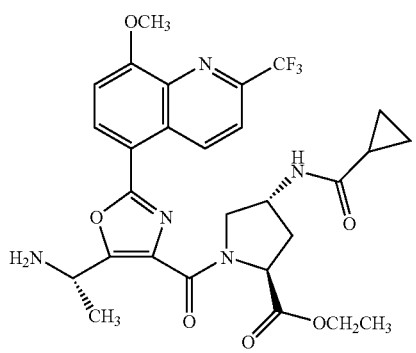

Compound A comprising the steps of:
e) adding toluene and methanol to Compound A and xinafoic acid and mixing, forming a slurry;
f) heating said slurry to about 62° C. while mixing, affording a homogeneous mixture;
g) distilling said homogeneous mixture atmospherically, cooling distilled mixture to about 50° C., seeding said distilled mixture with Compound A Form 1 seeds, resulting in crystals in a slurry;
h) stirring said slurry for about 30 minutes at about 50° C. and cooling the slurry to about 10° C.;
i) adding additional toluene to the cooled slurry and vacuum distilling, then adding additional toluene and stirring for about 20 minutes at about 20° C. forming solid material;
j) collecting resulting solids using agitated dryer under vacuum forming a wet cake; washing said wet cake with toluene and drying: at about 50° C. for about 3 hours without agitation, then about 80° C. for about 12 hours with about 20 R.P.M. agitation, then about 80° C. for about 12 hours with about 60 R.P.M. agitation, all under vacuum.

29. A process for preparing the polymorph Form 1 of claim 10 from

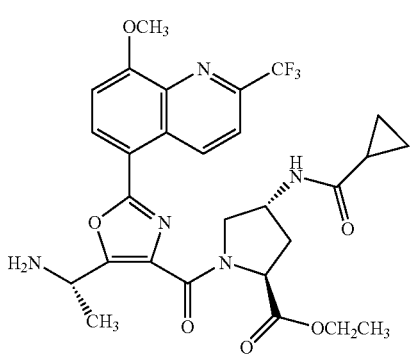

Compound A k) comprising the steps of: dissolving Compound A and xinafoic acid in hot methanol separately;
l) filtering both of the hot solutions and mixing the two solutions;
m) refluxing the mixture and distilling out the excess methanol; and
n) cooling the mixture to 0° C. forming a precipitate and filtering the Form 1 crystals.

30. An inhalable pharmaceutical composition comprising a crystalline polymorph of Form 1 of claim 10 and at least one pharmaceutically acceptable excipient or carrier.

31. A purified form of the polymorph of Form 1 of claim 10.

32. A method of treating upper or lower obstructive diseases of the airways in a patient in need of such treatment comprising administering to said patient by inhalation an effective amount of a polymorph of Form 1 of claim 10.

33. A process for preparing the polymorph Form 2 of claim 10 from

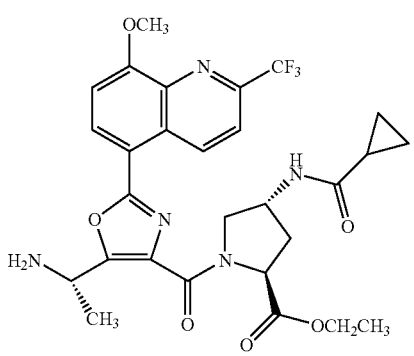

Compound A comprising the steps of:
o) dissolving Compound A in hot methanol and adding xinafoic acid while continuing to heat the mixture;
p) adding water, and heating the mixture to near boiling;
q) filtering the hot mixture, then cooling slowly to room temperature and allowing the mixture to stand at room temperature overnight until Form 2 crystals precipitate; and
r) cooling the filtrate to 0° C. and filtering the Form 1 crystals.

34. An inhalable pharmaceutical composition comprising a crystalline polymorph of Form 2 of claim 10 and at least one pharmaceutically acceptable excipient or carrier.

35. A purified form of the polymorph of Form 2 of claim 10.

36. A method of treating upper or lower obstructive diseases of the airways in a patient in need of such treatment comprising administering to said patient by inhalation an effective amount of a polymorph of Form 2 of claim 10.

37. A process for preparing the Dihydrate Form 1 of claim 10 from xinafoate salt polymorph Form 1 of Compound A:

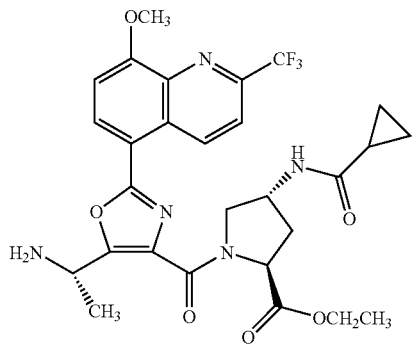

Compound A comprising the steps of:
r) Suspending Form I polymorph xinafoate salt of Compound A in a mixture of water and methanol;
s) the suspension was stirred for 21 hours, solids were isolated by centrifugation of the suspension then decanting off the supernatant;
t) Solids were dried under vacuum at room temperature.

38. An inhalable pharmaceutical composition comprising a crystalline of Dihydrate Form 1 of claim 10 and at least one pharmaceutically acceptable excipient or carrier.

39. A purified form of the crystalline Dihydrate Form 1 of claim 10.

40. A method of treating upper or lower obstructive diseases of the airways in a patient in need of such treatment comprising administering to said patient by inhalation an effective amount of Dihydrate Form 1 of claim 10.

41. A process for preparing the polymorph Form 3 of claim 10 from

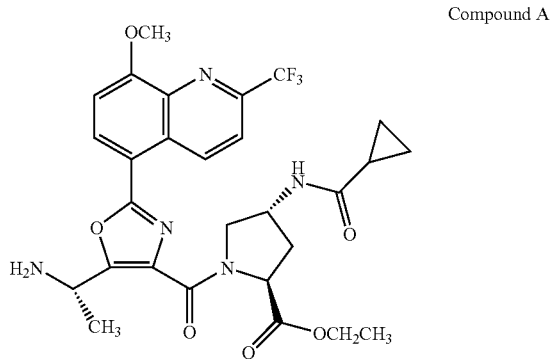

Compound A comprising the steps of:
u) combining a mixture of compound A and xinafoic acid in 2-propanol;
v) heat mixture to reflux and add more 2-propanol; hold mixture at reflux for 1 hour then cooled to room temperature;
w) filter mixture, wash solids with 2-propanol, dry under vacuum.

42. An inhalable pharmaceutical composition comprising a crystalline polymorph of Form 3 of claim 10 and at least one pharmaceutically acceptable excipient or carrier.

43. A purified form of the polymorph of Form 3 of claim 10.

44. A method of treating upper or lower obstructive diseases of the airways in a patient in need of such treatment comprising administering to said patient by inhalation an effective amount of a polymorph of Form 3 of claim 10.

* * * * *